(12) United States Patent
Kolb et al.

(10) Patent No.: US 8,486,372 B2
(45) Date of Patent: *Jul. 16, 2013

(54) CYCLIC AZAPEPTIDES AS INTEGRIN MARKERS AND METHODS OF USING

(75) Inventors: Hartmuth C. Kolb, Playa Del Rey, CA (US); Kai Chen, San Gabriel, CA (US); Joseph C. Walsh, Pacific Palisades, CA (US); Dhanalakshmi Kasi, Los Angeles, CA (US); Vani P. Mocharla, Los Angeles, CA (US); Gang Chen, Redondo Beach, CA (US); Qianwa Liang, Hacienda Heights, CA (US); Tieming Zhao, Los Angeles, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 53 days.

This patent is subject to a terminal disclaimer.

(21) Appl. No.: 13/113,580

(22) Filed: May 23, 2011

(65) Prior Publication Data

US 2011/0256057 A1    Oct. 20, 2011

Related U.S. Application Data

(62) Division of application No. 12/180,444, filed on Jul. 25, 2008, now Pat. No. 8,043,601.

(60) Provisional application No. 60/962,264, filed on Jul. 27, 2007.

(51) Int. Cl.
*A61B 5/055* (2006.01)

(52) U.S. Cl.
USPC ......... 424/9.3; 424/1.11; 424/1.65; 424/1.69; 424/1.81; 424/1.85; 424/1.89; 424/9.1; 424/9.2; 514/1.1

(58) Field of Classification Search
USPC ............... 424/1.11, 1.65, 1.69, 1.81, 1.85, 424/1.89, 9.1, 9.2, 9.3, 9.4, 9.5, 9.6, 9.7, 424/9.8; 514/1, 1.1; 530/300, 316, 317, 331, 530/333, 334, 338
See application file for complete search history.

(56) References Cited

U.S. PATENT DOCUMENTS

| | | | |
|---|---|---|---|
| 7,666,392 B2 * | 2/2010 | Kolb et al. | 424/9.1 |
| 8,043,601 B2 * | 10/2011 | Kolb et al. | 424/1.89 |
| 8,133,472 B2 * | 3/2012 | Kolb et al. | 424/1.69 |

* cited by examiner

*Primary Examiner* — D L Jones
(74) *Attorney, Agent, or Firm* — Joshua Ryan

(57) ABSTRACT

The present application is directed to radiolabeled cyclic polyazapeptides, pharmaceutical compositions comprising radiolabeled cyclic polyazapeptides, and methods of using the radiolabeled cyclic polyazapeptides. Such polyazapeptides can be used in imaging studies, such as Positron Emitting Tomography (PET) or Single Photon Emission Computed Tomography (SPECT).

19 Claims, 2 Drawing Sheets

BINDING AFFINITY COMPARISON OF c(RGDfK), RGD-C2, AND COMPOUND 7 USING SURFACE PLASMON RESONANCE ASSAY.

BINDING AFFINITY COMPARISON OF c(RGDfK), RGD-C2, AND COMPOUND 7 USING CELL-BASED INTEGRIN $\alpha_v \beta_3$ BINDING COMPETITION ASSAY.

CYCLIC AZAPEPTIDES AS INTEGRIN MARKERS AND METHODS OF USING

CROSS-REFERENCE TO RELATED APPLICATION

This application claims the benefit of U.S. Provisional Application No. 60/962,264, filed Jul. 27, 2007, the disclosure of which is incorporated herein in its entirety. This application is a divisional application of U.S. Ser. No. 12/180,444, filed on Jul. 25, 2008, the disclosure of which is incorporated by reference in its entirety.

FIELD OF THE INVENTION

The present application is directed at radiolabeled cyclic polyazapeptides (or cycloazapeptides), pharmaceutical compositions comprising radiolabeled cyclic polyazapeptides, and methods of using the radiolabeled cycloazapeptides. The present application is further directed to methods of preparing the radiolabeled cycloazapeptides and non-radiolabeled cycloazapeptides. Such radiolabeled cycloazapeptides may be used in imaging studies, such as Positron Emitting Tomography (PET) or Single Photon Emission Computed Tomography (SPECT).

In one embodiment, the present application discloses the preparation and use of radiolabeled cycloazapeptide analogs for imaging integrins (e.g., integrin $\alpha_v\beta_3$) in vivo. A series of potential integrin cycloazapeptides may be prepared using Arg-Gly-Asp (RGD) sequence as a binding motif. In another embodiment, click chemistry may be utilized to attach a radiolabel to cycloazapeptides that contain an RGD fragment. In another embodiment, the cycloazapeptides may further comprise hydrophilic linkages, such as oligo- or poly-ethyleneglycol ("PEG") moieties, polar amino acid moieties, sugars or sugar mimetics, such as cyclohexane diols or polyols. One advantage disclosed in the present application is a click chemistry labeling step that is easy to perform, and that quickly provides high yields of radiolabeled products that are easy to purify. The binding affinities of the radiolabeled cycloazapeptide analogs for different integrins have been determined using biochemical in vitro assays, such as surface plasmon resonance assay or cell-based binding assay. The click chemistry-derived integrin ligands of the present application display surprisingly high binding affinities to the biological target, and demonstrate very favorable pharmacokinetic behavior in mice (e.g. high tumor uptake and fast clearance through predominantly renal routes).

BACKGROUND OF THE INVENTION

Non-invasive molecular imaging plays a key role in detection of disease by characterizing and measuring biological processes at the molecular level. A number of medical diagnostic procedures, including PET and SPECT utilize radiolabeled compounds. PET and SPECT are very sensitive techniques and require small quantities of radiolabeled compounds, called tracers. The labeled compounds are transported, accumulated and converted in vivo in exactly the same way as the corresponding non-radioactively compound. Tracers or probes, can be radiolabeled with a radionuclide useful for PET imaging. Such radionuclide may include $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$ and $^{131}I$, or with a radionuclide useful for SPECT imaging, such as $^{99}Tc$, $^{75}Br$, $^{61}Cu$, $^{153}Gd$, $^{125}I$, $^{131}I$ and $^{32}P$.

PET creates images based on the distribution of molecular imaging tracers carrying positron-emitting isotopes in the tissue of the patient. The PET method has the potential to detect malfunctions on a cellular level in the investigated tissues or organs. PET has been used in clinical oncology, for the imaging of tumors and metastases, and has been used for diagnosis of certain brain diseases, as well as for mapping brain and heart function. Similarly, SPECT can be used to complement any gamma imaging study, where a true 3D representation can be helpful, for example, imaging tumor, infection (leukocyte), thyroid or bones.

The formation of new blood vessels sprouting from existing blood vessels, is a fundamental process, known as angiogenesis, associated with tumor progression. Angiogenesis is regulated by a balance between pro-angiogenic factors, such as vascular endothelial growth factor (VEGF), epidermal growth factor (EGF), fibroblast growth factor (FGF), and anti-angiogenic molecules, such as angiostatin and endostatin. Most tumors begin growing as avascular dormant nodules until they reach steady-state populations of proliferating and apoptosing cells. Angiogenesis starts with perivascular detachment and vessel dilation, followed by angiogenic sprouting, new vessel formation, maturation, and the recruitment of perivascular cells. Blood vessel formation continues as the tumor grows, feeding on hypoxic and necrotic areas of the tumor for essential nutrients and oxygen. This multi-step process offers several targets for the development of tumor angiogenic and metastatic diagnostics.

Integrins, are largely responsible for cell-cell and cell-matrix interactions, and are one of the main classes of receptors regulating tumor metastasis and angiogenesis. In addition to having adhesive functions, integrins transduce messages via various signaling pathways influencing proliferation and apoptosis of both tumor cells, and activated endothelial cells. Research has shown that integrins are a family of adhesion molecules consisting of two noncovalently bound transmembrane subunits ($\alpha$ and $\beta$). Both subunits are type I membrane proteins with large extracellular segments that pair to create heterodimers with distinct adhesive capabilities. In mammals, 18$\alpha$ and 8$\beta$ subunits assemble into 24 different receptors. One prominent member of this receptor class is the integrin $\alpha_v\beta_3$ receptor. The special role of integrin $\alpha_v\beta_3$ in tumor invasion and metastasis arises from its ability to recruit and activate matrix metalloproteinases 2 (MMP-2) and plasmin, which degrade components of the basement membrane and interstitial matrix. It has been demonstrated that tumor expression of integrin $\alpha_v\beta_3$ correlates well with tumor progression in several malignancies such as melanoma, glioma, breast cancer, and ovarian cancer. The receptor $\alpha_v\beta_3$ is not readily detectable in quiescent vessels but becomes highly expressed in angiogenic vessels, serving as an excellent molecular marker for tumor metastasis and angiogenesis imaging. Thus, the ability to noninvasively visualize and quantify integrin $\alpha_v\beta_3$ expression level will provide new opportunities to document tumor integrin expression, to properly select patients for anti-integrin treatment, and to monitor treatment efficacy in integrin-positive patients.

Based on the findings that several extracellular matrix proteins, such as vitronectin, fibrinogen, and thrombospondin interact with integrins via the amino acid sequence arginine-glycine-aspartic acid (RGD). Linear and cyclic peptides containing the RGD sequence have been extensively explored and tested. Kessler and co-workers [1] developed the pentapeptide cyclo(-Arg-Gly-Asp-D-Phe-Val-) ("c(RGDfV)") which showed both high affinity and selectivity for integrin $\alpha_v\beta_3$. To date, most integrin $\alpha_v\beta_3$ targeted PET studies have utilized the radiolabeling of c(RGDfV)-based antagonists due to their high binding affinities which range from nanomolar to subnanomolar range for monomeric and multimeric c(RGDfV) respectively. In particular, most efforts [2-4] are focused on the modification of the linkage connecting cyclic RGD peptide to the radionuclide. Currently, [$^{18}$F]Galacto-RGD [5-7] represents the most promising integrin marker in the clinical trial arena. Despite its successful translation into clinical trials, several key issues remain to be resolved. As a monomeric RGD peptide tracer, it has a relatively low tumor targeting efficacy. In addition, its clinical utility is severely limited because of its relatively low integrin binding affinity, modest tumor standard uptake values, and unfavorable pharmacokinetic behavior. Therefore, tumors with low integrin expression levels may not be detectable. In addition, prominent tracer accumulation in the liver, kidneys, spleen, and intestines was observed in both preclinical models and human studies resulting in difficult visualization of abdomen lesions. To add to its imaging drawbacks, the synthetic preparation of the tracer is labor intensive, time consuming and inefficient, thereby limiting its widespread availability to clinicians.

Recently, a library of RGD-containing pseudopeptides has been synthesized [8]. These compounds are characterized by the replacement of the D-Phe-Val or the D-Phe-[NMe]Val dipeptide with a 6,5- and 7,5-fused bicyclic lactam. In comparison with D-Phe-Val or D-Phe-[NMe]Val dipeptide, bicyclic lactams show different reverse-turn mimetic properties that constrain the RGD sequence into different conformations and provide the required integrin activity and selectivity. While these cyclic peptides validate the use of conformationally constrained RGD peptides as integrin ligands, they cannot be used directly for PET imaging due to their difficult synthesis.

SUMMARY OF THE INVENTION

For successful imaging of RGD tracer, several key challenges still need to be identified and resolved. First, the pharmacokinetic behavior of the tracer is suboptimal due to multi-organ accumulation of the tracer. Although glycosylation of RGD improved the pharmacokinetic behavior to a certain degree, prominent tracer accumulation in the liver, kidneys, spleen, and intestines is still observed in both preclinical models and human studies, making lesion visualization in the abdominal region difficult. Second, a major drawback of the strategies examined by others is the employment of difficult, time consuming and inefficient radiolabeling protocols which severely limits the exploration of improved derivatives and the use of these imaging agents as standard clinical biomarkers. Third, most integrin $\alpha_v\beta_3$ targeted radiolabeling cycloazapeptides (or cyclic azapeptides or polyazapeptides) are limited to the natural or unnatural amino acid-based peptides.

The azapeptides, which are the basis for the present invention, carry a nitrogen atom in the α-position of the amino acid. This ensures a favorable confirmation as well as resistance to degradation by proteolytic enzymes. As disclosed herein, substitution of a natural or unnatural amino acid by an aza amino acid preserves the cyclic peptides' functional and structural integrity while providing enhance metabolic stability in vivo. Therefore, by using these modified cycloazapeptides, the issues associated with unfavorable pharmacokinetic behavior can be attenuated. To our knowledge, the azapeptide-functionalized cyclic peptides as integrin imaging agents described in the present application have not been explored.

To solve the problem of low signal to noise ratios in vivo, and unfavorable pharmacokinetic properties, a library of cyclic azapeptides was built using the RGD sequence as an integrin binding motif. The library of markers was screened for binding to integrins. The cycloazapeptides that displayed high binding affinities were selected for radiolabeling with positron-emitting isotopes or conjugation with appropriate linker moieties and radioactive isotopes such as [$^{18}$F]-fluorine for in vivo PET imaging. As disclosed herein, the present approach using click chemistry enabled rapid synthesis and testing of many different potential integrin ligands as candidate PET tracers.

In one embodiment, the present application discloses imaging agents effective for detecting angiogenic tumors in vivo. The labeled cycloazapeptides of the present application, contain polar residues on a pendant amino acid side chain and those polar residues are coupled with a moiety comprising a radionuclide via a 'click chemistry' linkage (i.e. a 1,4- or 1,5-disubstituted 1,2,3-triazole). These click chemistry-derived compounds are easy to both synthesize and radiolabel. The compounds demonstrate surprisingly high binding affinity to integrin $\alpha_v\beta_3$, and improved pharmacokinetic properties compared to cyclic polypeptides belonging to the same class. The imaging agents disclosed in the present application are useful markers for imaging integrins in vivo. In one embodiment, this application discloses a means for detecting blood vessel growth in certain cancers in vivo, as well as a means for monitoring the efficacy of cancer therapy. Since the imaging agent allows in vivo imaging of blood vessel growth in solid tumors, it enables personalized anti-angiogenesis cancer therapies.

DETAILED DESCRIPTION

The embodiments and aspects of the invention and the various features and advantageous details thereof are explained more fully with reference to the non-limiting embodiments, aspects and examples that are described and/or illustrated in the accompanying figures and detailed in the following description. It should be noted that the features of one embodiment or aspect may be employed with other embodiments as the skilled artisan would recognize, even if not explicitly stated herein. The examples used herein are intended merely to facilitate an understanding of ways in which the invention may be practiced and to further enable those of skill in the art to practice the embodiments of the present application. Accordingly, the examples and embodiments herein should not be construed as limiting the scope of the application, which is defined solely by the appended claims.

DEFINITIONS

Figure 1:
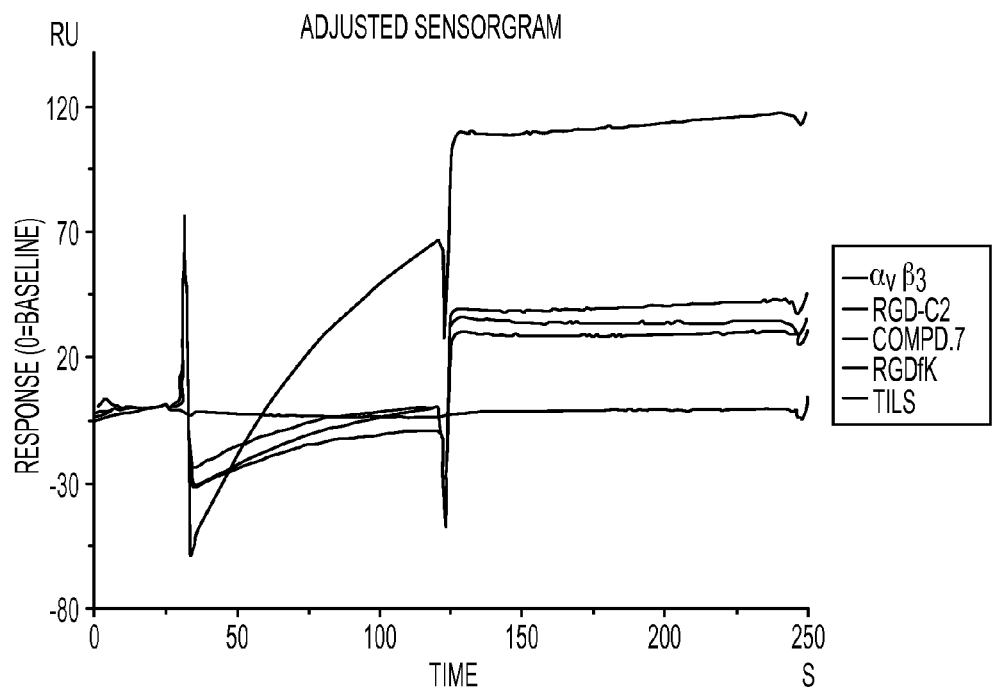
FIG. 1 is a graph of binding affinity determination of cyclo-peptides using surface plasmon resonance assay.
Figure 1:
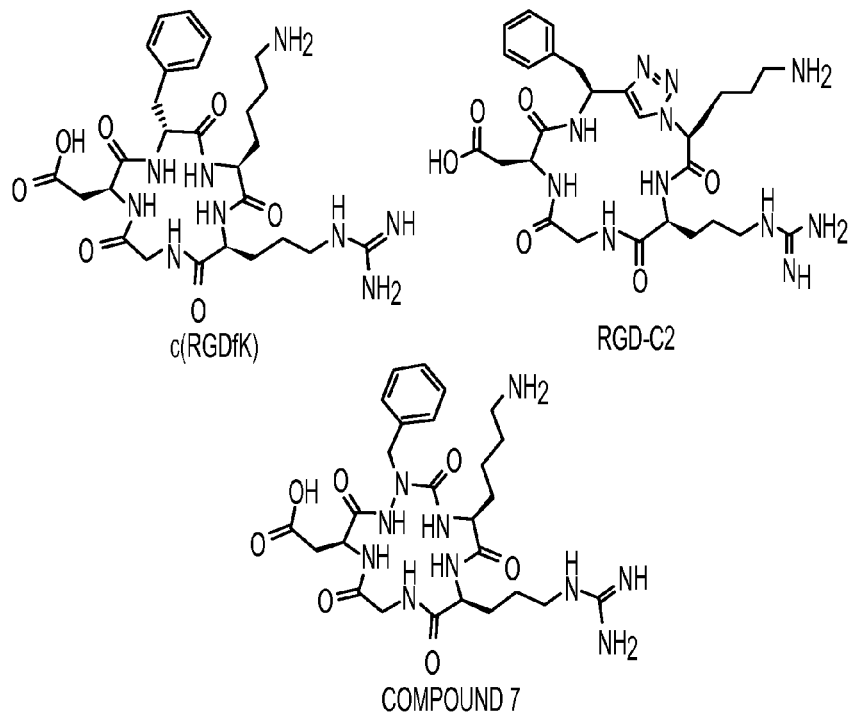

Unless specifically noted otherwise herein, the definitions of the terms used are standard definitions used in the art of organic and peptide synthesis and pharmaceutical sciences.

An "alkyl" group is a straight, branched, saturated or unsaturated, aliphatic group having a chain of carbon atoms, optionally with oxygen, nitrogen or sulfur atoms inserted between the carbon atoms in the chain or as indicated. Alkyl groups may be optionally substituted. A $(C_1-C_6)$alkyl, for example, includes each of the alkyl groups that have a chain of between 1 and 6 carbon atoms, and include, for example, the groups methyl (i.e., $C_1$ alkyl), ethyl ($C_2$ alkyl), propyl ($C_3$ alkyl), isopropyl ($C_3$ alkyl), vinyl, allyl, 1-propenyl, isopropenyl, ethynyl, 1-propynyl, 2-propynyl, 1,3-butadienyl ($C_4$ alkyl), penta-1,3-dienyl ($C_5$ alkyl), and the like. An alkyl group, such as a "$C_1$-$C_6$ alkyl," that forms a part of a group or linker is a divalent alkyl group, and also may be referred to as an "alkylene" or "alkylenyl" group. Similarly, an alkenyl group, alkynyl group, aryl group, etc in a structure that is shown as a divalent group may be referred to as an alkenylenyl, alkynylenyl, arylenyl group, respectively. The representation of "($C_{1-3}$)alkyl", for example, is used interchangeably with "$C_1$-$C_3$alkyl" to mean the same.

An alkyl as noted with another group such as an aryl group, represented as "arylalkyl" for example, is intended to be a straight, branched, saturated or unsaturated aliphatic divalent group with the number of atoms indicated in the alkyl group (as in ($C_1$-$C_6$)alkyl, for example) and/or aryl group or when no atoms are indicated means a bond between the aryl and the alkyl group. Nonexclusive examples of such group include benzyl, phenylethyl and the like.

An "alkylene" group or "alkylenyl" group is a straight, branched, saturated or unsaturated aliphatic divalent group with the number of atoms indicated in the alkyl group; for example, a —($C_1$-$C_3$)alkylene- or —($C_1$-$C_3$)alkylenyl-.

The term "alkenyl" refers to unsaturated groups which contain at least one carbon-carbon double bond and includes straight-chain, branched-chain and cyclic groups. Alkene groups may be optionally substituted. Exemplary groups include 1-butenyl, 2-butenyl, 3-butenyl, isobutenyl, 1-propenyl, 2-propenyl and ethenyl.

The term "alkoxy" or "alkyloxy" includes linear or branched alkyl groups that are attached to divalent oxygen. The alkyl group is as defined above. Examples of such substituents include methoxy, ethoxy, t-butoxy and the like. The term "alkoxyalkyl" refers to an alkyl group that is substituted with one or more alkoxy groups. Alkoxy groups may be optionally substituted. The term "aryloxy" refers to an aryl group that is attached to an oxygen, such as phenyl-O—, etc.

The term "alkynyl" refers to unsaturated groups which contain at least one carbon-carbon triple bond and includes straight-chain, branched-chain and cyclic groups. Alkyne groups may be optionally substituted. Exemplary groups include 1-butynyl, 2-butynyl, 3-butynyl, 1-propynyl, 2-propynyl and ethynyl.

"Aryl" means one or more aromatic rings, each of which may comprise 5 or 6 core carbon atoms. Aryl includes multiple aryl rings that may be fused, as in naphthyl or non-fused, as in biphenyl. Aryl rings may also be fused or non-fused with one or more cyclic hydrocarbon, heteroaryl or heterocyclic rings. As used herein, "aryl" includes heteroaryl.

The term "aza amino acid" or "azapeptide" as used herein, refers to a natural or unnatural amino acid, or peptide, wherein the carbon atom in the α-position (the ʄ-carbon or alpha carbon) of the amino acid is replaced with a nitrogen atom. In an azapeptide or cycloazapeptide, one or more of the alpha carbon of one or more amino acid in the peptide may be replaced with a nitrogen atom. In the cycloazapeptides of the present application, where more than one of the amino acids are aza amino acids, such as 2, 3, 4 or 5 aza amino acids, the aza amino acid(s) in the peptide may be adjacent or non-adjacent to each other or may be in alternating positions in the peptide. In certain aspects, the cycloazapeptides comprise one aza amino acid.

The term "carbocycle" (or carbocyclyl) as used herein refers to a $C_3$ to $C_{14}$ monocyclic or bicyclic, saturated, partially saturated or aromatic ring. Bonds in a carbocycle depicted as " - - - " indicate bonds that can be either single or double bonds. Carbocycles may be optionally substituted. Non-exclusive examples of carbocycle include cyclopropane, cyclobutane, cyclopentane, cyclohexane, cycloheptane, cyclopentene, cyclohexene, cycloheptene, cyclooctene, benzyl, naphthene, anthracene, phenanthracene, biphenyl and pyrene.

The term "halo" or "halogen" means fluoro, chloro, bromo and iodo.

A "heterocycle" or "heterocyclyl" is a carbocycle group wherein one or more of the atoms forming the ring is a heteroatom that is a N, O or S. The heterocycle may be saturated, partially saturated or aromatic. Bonds in a heterocycle depicted as " - - - " indicate bonds that can be either single or double bonds. Heterocycles may be optionally substituted. Non-exclusive examples of heterocyclyl (or heterocycle) include triazoles (e.g., 1,2,3-triazoles), piperidyl, 4-morpholyl, 4-piperazinyl, pyrrolidinyl, 1,4-diazaperhydroepinyl, acetonidyl-4-one, 1,3-dioxanyl, thiophenyl, furanyl, pyrrolyl, pyrazolyl, pyridinyl, pyrimidinyl, pyridazinyl, pyranyl and the like.

As an example, for the fragment that is represented as:

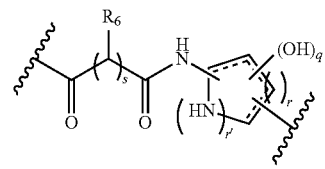

wherein r', r, s and q are all 1, for example, the fragment is intended to include the following non-limiting, representative structures:

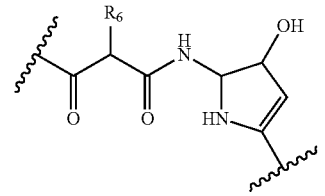

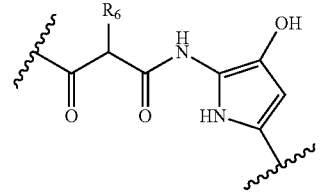

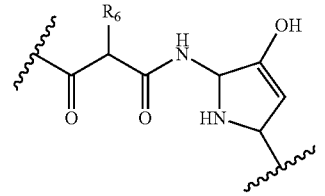

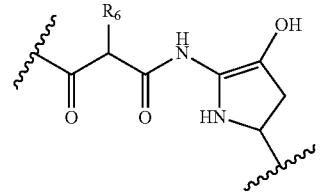

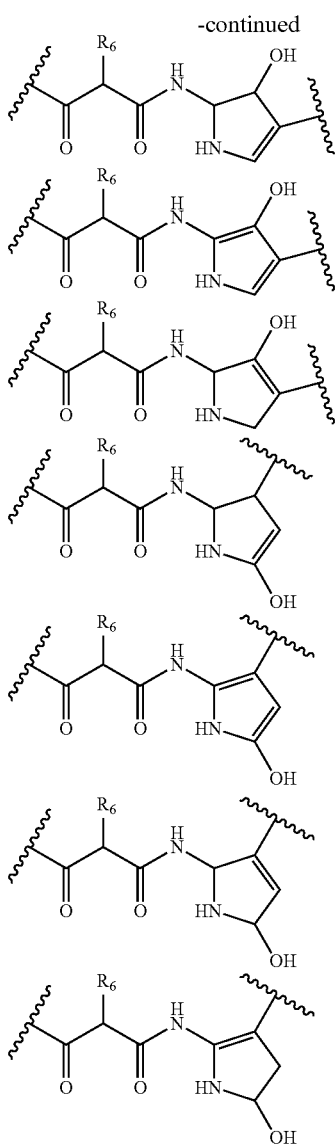

In the case of the above compounds that are represented by enol forms of the cyclic structures, the corresponding stable keto tautomers are also intended to be included.

The term "optionally substituted" or "substituted" refers to the specific group wherein one to four hydrogen atoms in the group may be replaced by one to four substituents, independently selected from alkyl, aryl, alkylaryl, hydroxy, alkoxy, aryloxy, perhaloalkoxy, heterocyclyl, azido, amino (such as —$NH_2$, —$NH(C_1-C_{10})$alkyl, —$N[(C_1-C_{10})$alkyl$]_2$, —NHaryl, —N(aryl)($C_1-C_{10}$)alkyl, etc. . . . ), guanidino, amidino, halo, alkylthio, oxo (—C(O)—), acylalkyl, carboxy esters, carboxyl, carboxamido, nitro, acyloxy, aminoalkyl, alkylaminoaryl, alkylaminoalkyl, alkoxyaryl, arylamino, phosphono, sulfonyl, carboxamidoaryl, hydroxyalkyl, haloalkyl, cyano, alkoxyalkyl and perhaloalkyl. In addition, the term "optionally substituted" or "substituted" in reference to $R_2$, $R_3$ or $R_7$ for example, includes groups substituted by one to four substituents, as identified above, that further comprises a positron or gamma emitter. Such positron emitters include, but are not limited to, $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$.

In certain aspects of the present application, for the radiolabeled compounds of the present application, a radionuclide may be attached to the azapeptide, for example, on any one or more of the variables X, Y, $R_2$, $R_3$ and $R_7$ of the compound of the present application, or wherein a 2-($^{18}$F-fluoroethyl)-, 2-($^{18}$F-fluoromethyl)-, a $^{11}$C-methoxy-group that is attached to a compound that is Cyclo-(R-G-D-L1-L2), formula Z, or Formula I, II, III or IV, for example. The radionuclide may also be attached to any one or more of the variables X, Y, $R_2$, $R_3$ and $R_7$ as a $^{18}$F-fluoroethyl-group, a $^{18}$F-fluoromethyl-group, a $^{18}$F-fluoroethoxy-group, a $^{11}$C-methoxy-group, a $^{18}$F-fluoropropyloxy-group and the like, a $^{123}$I, a $^{124}$I, a $^{125}$I or a $^{131}$I group, and the like. Unless otherwise noted, a compound represented as being substituted by an atom, such as the generic representation by the atom fluorine in F—$CH_2CH_2$— or F—$CH_2CH_2O$— as attached to a compound of that is Cyclo-(R-G-D-L1-L2), formula Z, or Formula I, II, III or IV, for example, is intended to cover both the naturally occurring element $^{19}$F (fluorine-19) as well as the $^{18}$F (fluorine-18) isotope(s) of the element itself.

The term "radionuclide" or "radioactive isotope" refers to isotopes exhibiting radioactive decay (i.e., emitting positrons) and radiolabeling agents comprising a radioactive isotope (e.g., [$^{11}$C]methane, [$^{11}$C]carbon monoxide, [$^{11}$C]carbon dioxide, [$^{11}$C]phosgene, [$^{11}$C]urea, [$^{11}$C]cyanogen bromide, as well as various acid chlorides, carboxylic acids, alcohols, aldehydes and ketones containing carbon-11). Such isotopes are also referred to in the art as radioisotopes or radionuclides. Radioactive isotopes are named herein using various commonly used combinations of the name or symbol of the element and its mass number (e.g., $^{18}$F, F-18, or fluorine-18). Exemplary radioactive isotopes include I-124, F-18 fluoride, C-11, N-13, and O-15, which have half-lives of 4.2 days, 110 minutes, 20 minutes, 10 minutes and 2 minutes, respectively. The radioactive isotope is preferably dissolved in an organic solvent, such as a polar aprotic solvent. Preferably, the radioactive isotopes used in the present method include F-18, C-11, I-123, I-124, I-127, I-131, Br-76, Cu-64, Tc-99m, Y-90, Ga-67, Cr-51, Ir-192, Mo-99, Sm-153 and Tl-201. Other radioactive isotopes that may be employed include: As-72, As-74, Br-75, Co-55, Cu-61, Cu-67, Ga-68, Ge-68, I-125, I-132, In-111, Mn-52, Pb-203 and Ru-97.

For $^{11}$C-labeled compounds, the labeled compound may be prepared by the alkylation or methylation of a hydroxyl group, such as with [$^{11}$C]$CH_3$I to provide the corresponding C-11 labeled methoxy derivative. For example, such a process is represented by the reaction of the flavone derivative shown below.

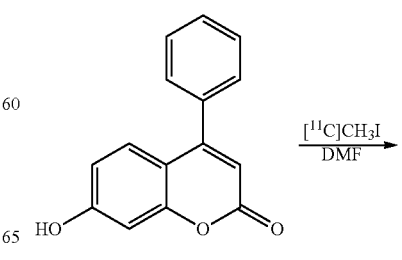

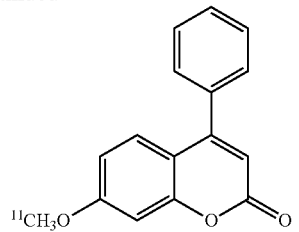

Other methods of preparing radiolabeled ligands are well known in the art. Example of such methods are disclosed in, for example: 1) Jewett, D. M. (1992) A Simple Synthesis of [$^{11}$C]Methyl Triflate Appl. Radiat. Isot. 43, 1383-1385; 2) Crouzel, C. Langstrom, B., Pike, V. W., and Coenen, H. H. (1987) Recommendations for a practical production of [$^{11}$C]methyl iodide Appl. Radiat. Isot. Int. J. Appl. Instrum. Part A 38, 601-603; Dannals, R. F., Ravert, H. T.; 3) Wilson, A. A. (1990) Radiochemistry of Tracers for Neurotransmitter Receptor Studies. In: Quantitative Imaging: Neuroreceptors, Neurotransmitters, and Enzymes. (Edited by Frost), J. J. Wagner Jr., H. N. pp. 19-35, Raven Press, New York; 4) Jewett, D. M., Manger, T. J., and Watkins, G. L. (1991) Captive Solvent Methods for Fast Simple Carbon-11 Radioalkylations. In: New Trends in Radiopharmaceutical Synthesis, Quality Assurance and Regulatory Control (Edited by Emran, A. M.) pp. 387-391. Plenum Press, New York; 5) Marazano, C., Maziere, M., Berger, G., and Comar, D. (1977) Synthesis of methyl iodide-$^{11}$C and formaldehyde-$^{11}$C Appl. Radiat. Isot. 28, 49-52; 6) Watkins, G., Jewett, D., Mulholland, G., Kitbourn, M., and Toorongian, S. (1988) A Captive Solvent Method for Rapid N—[$^{11}$C]Methylation of Secondary Amides Application to the Benzodiazepine, 4'-Chlorodiazepam (RO5-4864) Appl. Radiat. Isot. 39, 441-444; and 7) Wilson, A. A., DaSilva, J. N., and Houle, S. (1996) In vivo evaluation of [$^{11}$C] and [$^{15}$F]-labeled cocaine analogues as potential dopamine transporter ligands for positron emission tomography Nucl. Med. Biol. 23, 141-146. The subject matter of all references cited herein are incorporated herein by reference in their entirety.

As used herein, the term "side chain" of a natural or unnatural amino acid refers to "Q" group in the amino acid formula, as exemplify with NH$_2$CH(O)CO$_2$H.

As used herein, the term "polar amino acid moiety" refers to the side chain, Q, of a polar natural or unnatural amino acid. Polar natural amino acids include but are not limited to arginine, asparagine, aspartic acid, cysteine, glutamic acid, glutamine, histidine and lysine.

As used herein, "natural amino acid" refers to the naturally occurring amino acids: glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine and lysine. Accordingly, a derivative of an amino acid may be an ester, such as a (C$_1$-C$_6$)alkyl ester, a protected amino acid such as an N-acetyl amino acid, and combinations thereof.

The term "unnatural amino acid" refers to any derivative of a natural amino acid including for example D and L forms, and α- and β-amino acid derivatives. It is noted that certain amino acids, e.g., hydroxyproline, that are classified as a non-natural amino acid herein, may be found in nature within a certain organism or a particular protein. The following non-exclusive examples of non-natural amino acids and amino acid derivatives may be used according to the application (common abbreviations in parentheses): β-alanine (β-ALA), γ-aminobutyric acid (GABA), ornithine, 2-aminobutyric acid (2-Abu), α,β-dehydro-2-aminobutyric acid (8-AU), 1-aminocyclopropane-1-carboxylic acid (ACPC), aminoisobutyric acid (Aib), γ-carboxyglutamic acid, 2-amino-thiazoline-4-carboxylic acid, 5-aminovaleric acid (5-Ava), 6-aminohexanoic acid (6-Ahx), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-NH$_2$-Phe), biphenylalanine (Bip), para-bromophenylalanine (4-Br-Phe), ortho-chlorophenylalanine] (2-Cl-Phe), meta-chlorophenylalanine (3-Cl-Phe), para-chlorophenylalanine (4-Cl-Phe), meta-chlorotyrosine (3-Cl-Tyr), para-benzoylphenylalanine (Bpa), tert-butylglycine (TLG), cyclohexylalanine (Cha), cyclohexylglycine (Chg), 2,3-diaminopropionic acid (Dpr), 2,4-diaminobutyric acid (Dbu), 3,4-dichlorophenylalanine (3,4-Cl$_2$-Phe), 3,4-difluororphenylalanine (3,4-F$_2$-Phe), 3,5-diiodotyrosine (3,5-I$_2$-Tyr), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), 5-hydroxytryptophan (5-OH-Trp), hydroxyproline (Hyp), para-iodophenylalanine (4-I-Phe), 3-iodotyrosine (3-I-Tyr), indoline-2-carboxylic acid (Idc), isonipecotic acid (Inp), meta-methyltyrosine (3-Me-Tyr), 1-naphthylalanine (1-Nal), 2-naphthylalanine (2-Nal), para-nitrophenylalanine (4-NO$_2$-Phe), 3-nitrotyrosine (3-NO$_2$-Tyr), norleucine (Nle), norvaline (Nva), ornithine (Orn), ortho-phosphotyrosine (H$_2$PO$_3$-Tyr), octahydroindole-2-carboxylic acid (Oic), penicillamine (Pen), pentafluorophenylalanine (F$_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th). Additionally, N-alkylated amino acids may be used, as well as amino acids having amine-containing side chains (such as Lys and Orn) in which the amine has been acylated or alkylated.

As used herein, "sugar moiety" refers to an oxidized, reduced or substituted saccharide monoradical or diradical covalently attached via any atom(s) of the sugar moiety. Representative sugars include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(3-desmethyl-α-L-vancosaminyl)-β-D-glucopyranose, sucrose, lactose, or maltose; derivatives such as acetals, amines, acylated, sulfated and phosphorylated sugars; and oligosaccharides having from 2 to 10 sugar units.

As used herein, a hexose structure that is represented below, for example:

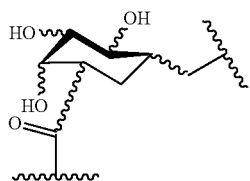

showing the curved lines (∿∿∿) is intended to represent a structure having the stereochemistry of any one of the natural sugars, including allose, altrose, galactose, glucose, gulose, idose, mannose, talose, etc. . . . , as well as their unnatural and synthetic hexose analogs and derivatives, and also includes certain sugar moieties.

As used herein, "sugar mimetic" refers to carbocycles or heterocycles substituted with at least one hydroxyl group. Such carbocycle groups include, but are not limited to cyclohexane, cyclohexene, cyclopentane and cyclobutane; such heterocycles include, but are not limited to, pyrrolidine and piperidine.

As used herein, "PEG moiety" refers to a fragment of poly(ethylene glycol), a polymer of ethylene oxide. PEG has the formula:

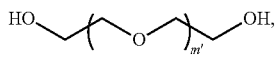

where m' is an integer between 1 and 200, alternatively between 1 and 110 or between 10 and 90; m' can also be an integer between 50 and 75. Alternately m' can be an integer between 1 and 50 or between 1 and 15 or between 1 and 10. As used herein, the clauses defining a variable as between two numbers, such as "an integer between 1 and 10" for example, also include 1 and 10.

"Linker" as used herein refers to a chain comprising 1 to 200 atoms and may comprise atoms or groups, such as C, —NR—, O, S, —S(O)—, —S(O)$_2$—, CO, —C(NR)—, a PEG moiety, and the like, and combinations thereof as defined herein, and wherein R is H or is selected from the group consisting of $(C_{1-10})$alkyl, $(C_{3-8})$cycloalkyl, aryl$(C_{1-5})$alkyl, heteroaryl$(C_{1-5})$alkyl, amino, aryl, heteroaryl, hydroxy, $(C_{1-10})$alkoxy, aryloxy, heteroaryloxy, each substituted or unsubstituted. In one aspect, the linker may be a chain comprising 1 to 100 atoms, 2 to 50 atoms or 2 to 30 atoms, and may comprise of 1, 2 or 3 adjacent or non-adjacent atoms or groups, such as C, —NR—, O, S, —S(O)—, —S(O)$_2$—, CO, —C(NR)— and the like, and wherein R is H or is selected from the group consisting of $(C_{1-10})$alkyl, $(C_{3-8})$cycloalkyl, aryl$(C_{1-5})$alkyl, heteroaryl$(C_{1-5})$alkyl, amino, aryl, heteroaryl, hydroxy, $(C_{1-10})$alkoxy, aryloxy, heteroaryloxy, each substituted or unsubstituted. That is, for example, the linker may comprise of the groups: —CH$_2$—, —CH$_2$—CH$_2$—, —CH$_2$—O—CH$_2$—, —CH$_2$—CH$_2$—O—CH$_2$—CH$_2$—, —CH$_2$—NH—CH$_2$—, —CH$_2$—CH$_2$—NH—CH$_2$—CH$_2$—, —CH$_2$—NHC(O)—CH$_2$—, —CH$_2$—C(O)NH—CH$_2$—, —CH$_2$—C(O)—CH$_2$— etc. . . . . The linker chain may also comprise part of a saturated, unsaturated or aromatic ring, including monocyclic (e.g. a 1,5-cyclohexylenyl group, sugar mimetic, and sugar moiety), polycyclic and heteroaromatic rings (e.g. a 2,4-pyridinyl group etc. . . . ). As used herein, the term "linker" is a group that may be used to link interconnecting moieties such as —X—YR$_2$R$_3$, including linking a cyclic polypeptide moiety and a triazole moiety.

As used herein, where a divalent group, such as a linker, is represented by a structure -A-B—, as shown below, it is intended to also represent a group that may be attached in both possible permutations, as noted in the two structures below.

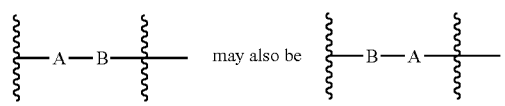

As used herein, the phrase "pharmaceutically acceptable carrier" refers to an excipient that may optionally be included in the compositions of the present application and that causes no significant adverse toxicological effects when administered in vivo.

As used herein, the term "patient" refers to any warm-blooded animal, such as a mouse, dog or human.

The compounds of the present application may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc or organic salts made from N, NT-dibenzylethylenediamine, chloroprocaine, choline, diethanolamine, ethylenediamine, meglumine-(N-methylglucamine) and procaine. Suitable formulations for each of these methods of administration may be found in, for example, Remington: The Science and Practice of Pharmacy, A. Gennaro, ed., 20th edition, Lippincott, Williams & Wilkins, Philadelphia, Pa.

Embodiments, Aspects and Variations of the Invention

The present application provides the following embodiments, aspects and variations:

In one embodiment, there is provided a cyclic azapeptide comprising the formula:

Cyclo-(R-G-D-L1-L2)

wherein L1 and L2 are each independently selected from the group consisting of an amino acid, amino acid derivative, aza-amino acid and an aza-amino acid derivative, provided that at least one of L1 and L2 is an aza-amino acid or an aza-amino acid derivative; or a pharmaceutically acceptable salt thereof, optionally in the form of a single stereoisomer or mixture of stereoisomers thereof. In one variations, L1 or L2 further comprises a radionuclide. In another variation of the azapeptide, the radionuclide is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$.

In another embodiment, there is provided a pharmaceutical composition comprising a therapeutically effective amount of a compound or composition comprising: a) a therapeutically effective amount of the above compound; and b) a pharmaceutically acceptable excipient. In another embodiment, there is provided a method of monitoring the level of integrin $\alpha_v\beta_3$ or visualizing integrin $\alpha_v\beta_3$ expression within a body of a patient, the method comprising: (a) administering to the patient a radiolabeled cycloazapeptide; and (b) employing a nuclear imaging technique selected from the group consisting of positron emission tomography (PET) and single photon emission computed tomography (SPECT) for monitoring or visualizing a distribution of the radiolabeled cycloazapeptide within the body or within a portion thereof; wherein the radiolabeled cycloazapeptide is of the formula:

Cyclo-(R-G-D-L1-L2)

wherein L1 and L2 are each independently selected from the group consisting of an amino acid, amino acid derivative, aza-amino acid and an aza-amino acid derivative, provided that at least one of L1 and L2 is an aza-amino acid or an aza-amino acid derivative; or a pharmaceutically acceptable salt thereof, optionally in the form of a single stereoisomer or mixture of stereoisomers thereof.

In another embodiment, there is provided a method for imaging of blood vessel growth in solid tumors based on expression of integrin $\alpha_v\beta_3$ within the body of a patient, the method comprising: (a) administering to the patient a radiolabeled cycloazapeptide; (b) employing a nuclear imaging technique selected from the group consisting of positron emission tomography (PET) and single photon emission computed tomography (SPECT) for imaging a distribution of the radiolabeled cycloazapeptide within the body or within a portion thereof; and c) correlating the distribution of the radiolabeled cycloazapeptide to the growth of blood vessels in solid tumors, wherein the radiolabeled cycloazapeptide is of the formula:

Cyclo-(R-G-D-L1-L2)

wherein L1 and L2 are each independently selected from the group consisting of an amino acid, amino acid derivative, aza-amino acid and an aza-amino acid derivative, provided that at least one of L1 and L2 is an aza-amino acid or an aza-amino acid derivative; or a pharmaceutically acceptable salt thereof, optionally in the form of a single stereoisomer or mixture of stereoisomers thereof.

In yet another embodiment, there is provided a cycloazapeptide of the formula Z:

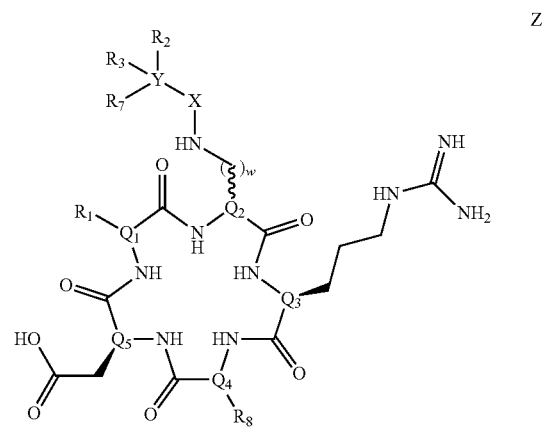

wherein: each $Q_1$, $Q_2$, $Q_3$, $Q_4$ and $Q_5$ is independently —CH— or N, provided that at least one of $Q_1$, $Q_2$, $Q_3$, $Q_4$ and $Q_5$ is N; $R_1$ is hydrogen or is selected from the group consisting of a side chain of a natural amino acid and a side chain of an unnatural amino acid; $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, alkoxyalkyl, aryl, carbocycle and heterocycle groups are each optionally substituted; $R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, arylalkylene, carbocycle and heterocycle groups are each optionally substituted; wherein $R_2$, $R_3$ and $R_7$ are not all H; $R_8$ is hydrogen or is selected from the group consisting of a side chain of a natural amino acid and a side chain of an unnatural amino acid; X is a 5 or 6-membered heterocycle or a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic and sugar moiety, or a combination thereof; Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic and sugar moiety; where at least one of X and Y is a 5 or 6-membered heterocycle; and w is 1, 2, 3, 4 or 5; or a pharmaceutically acceptable salt thereof, optionally in the form of a single stereoisomer or mixture of stereoisomers thereof. In one variation of the above cycloazapeptide, wherein any one of X, Y, $R_2$, $R_3$ and $R_7$ comprises a radionuclide selected from the group consisting of positron or gamma emitters. In another variation of the above, the radionuclide is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$.

In another embodiment, there is provided a cycloazapeptide of formula I:

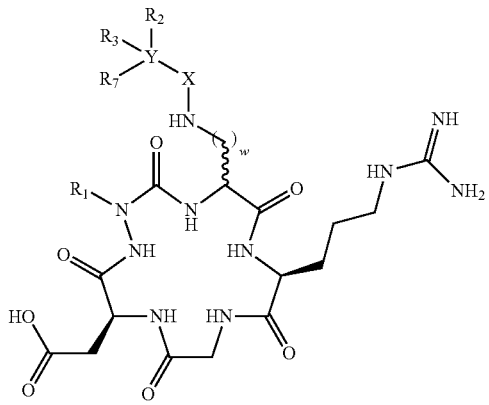

wherein: $R_1$ is hydrogen or is selected from the group consisting of a side chain of a natural amino acid and a side chain of an unnatural amino acid; $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, alkoxyalkyl, aryl, carbocycle and heterocycle groups are each optionally substituted; $R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, arylalkylene, carbocycle and heterocycle groups are each optionally substituted; wherein $R_2$, $R_3$ and $R_7$ are not all H; X is a 5 or 6-membered heterocycle or a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic and sugar moiety, or a combination thereof; Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic and sugar moiety; where at least one of X and Y is a 5 or 6-membered heterocycle; and w is 1, 2, 3, 4 or 5; or a pharmaceutically acceptable salt thereof, optionally in the form of a single stereoisomer or mixture of stereoisomers thereof.

As provided herein, the clause "X is a 5 or 6-membered heterocycle or a linker comprising a hydrophilic moiety selected from the group consisting of hydroxyl, carbonyl, sulfonamide, sulfonate, phosphate, polar amino acid moiety, PEG moiety, sugar mimetic, and sugar moiety, or a combination thereof" means that, for example, where X is a linker such as a $C_1$-$C_{10}$ alkylenyl group, the $C_1$-$C_{10}$ alkylenyl group may be substituted with a hydroxyl group; or X may be a linker that comprises a sugar mimetic as part of the linker; or X may be a $C_1$-$C_{10}$ alkylenyl group that comprises a carbonyl group in the linker, the $C_1$-$C_{10}$ alkylenyl group may be substituted with a hydroxyl group and comprises an adjacent or non-adjacent sugar mimetic as part of the $C_1$-$C_{10}$ alkylenyl group or the $C_1$-$C_{10}$ alkylenyl group may be substituted with a sugar mimetic (as a substituent), and the various combinations and permutations thereof.

In certain variations of each of the embodiments and aspects of the present application, the 5-membered heterocycle is a substituted 1,2,3-triazolyl group as disclosed herein.

In one embodiment of any of the aspects disclosed herein, Y is a 5 or 6-membered heterocycle; and X is a linker either comprising a sugar mimetic selected from the group consisting of a 4 to 6-membered carbocycle substituted with at least one hydroxyl group and a 5- to 6-membered heterocycle substituted with at least one hydroxyl group or comprising a sugar moiety selected from the group consisting of glucose and galactose. In another embodiment, X is a linker comprising a sugar mimetic selected from the group consisting of a hydroxylated cyclohexanyl group, a hydroxylated cyclopentanyl group, a hydroxylated pyrrolidinyl group, and a hydroxylated piperidinyl group. As provided herein, a "hydroxylated" group, such as a hydroxylated cyclohexanyl group, for example, comprises 1, 2, 3, 4 or 5 hydroxyl substituents (i.e., —OH) on the group. In yet another embodiment, Y is a 5 or 6-membered heterocycle; X is selected from the group consisting of:

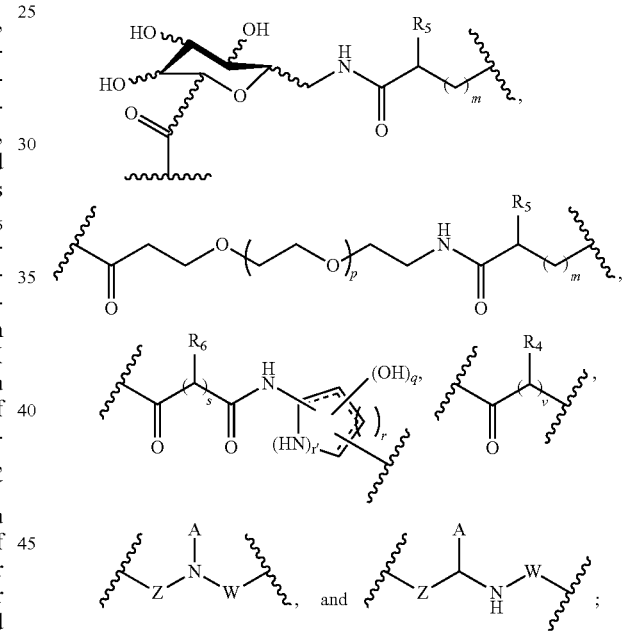

where Z is selected from the group consisting of:

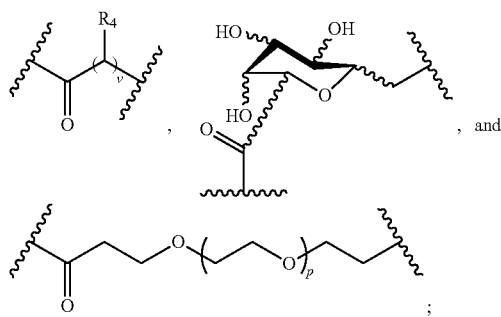

W is selected from the group consisting of:

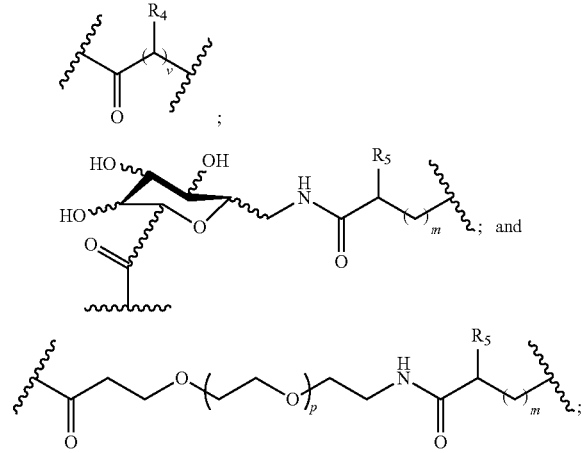

A is selected from the group consisting of:

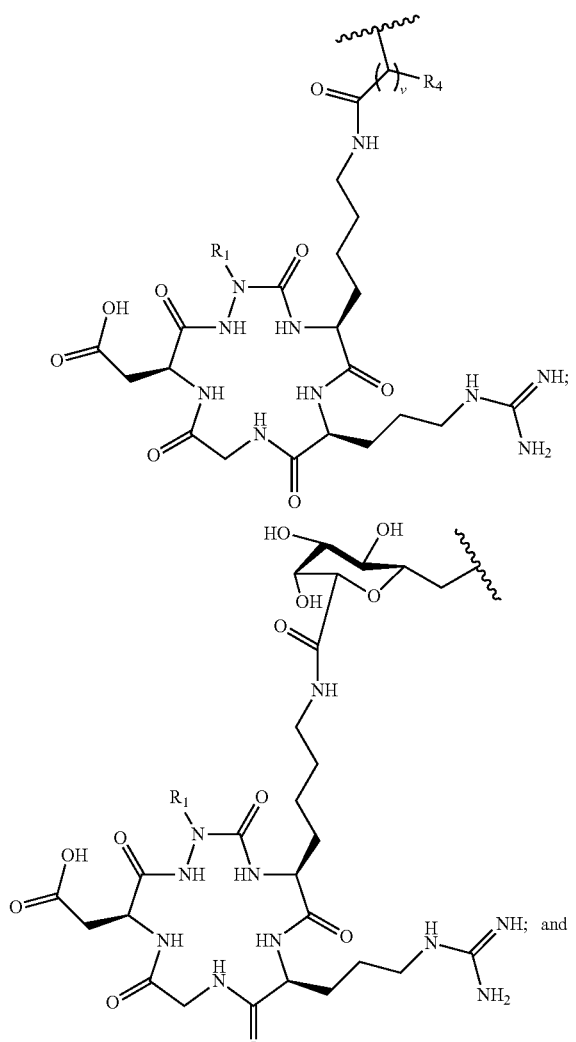

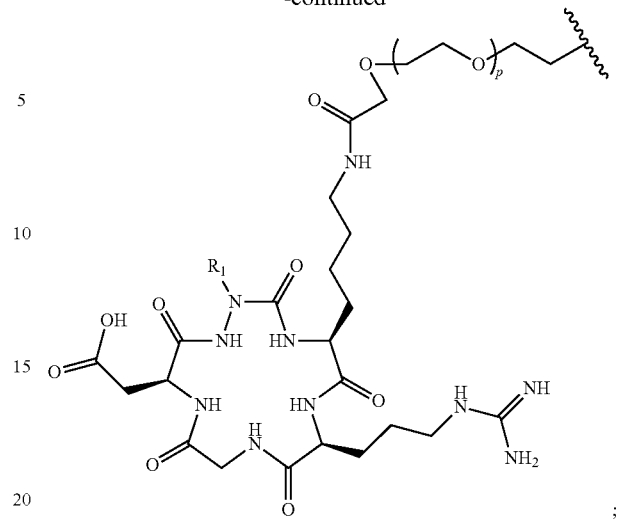

each $R_1$ is hydrogen or is independently selected from the group consisting of a side chain of a natural amino acid and a side chain of an unnatural amino acid;

each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$ alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl, and $C_1$-$C_6$-alkoxy-$C_1$-$C_6$-alkyl, wherein the alkyl, alkenyl, alkynyl, alkyloxy, and aryl-alkylene groups are each optionally substituted;

each v is 0, 1, 2, 3, or 4; m is 0, 1, 2, 3 or 4; p is an integer between 1 and 110; q is 1, 2, 3 or 4; r is 1, 2 or 3; r' is 0 or 1; s is 1, 2, 3 or 4; and the radionuclide is selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P; wherein the configuration of the chiral centers may be R or S or mixtures thereof.

In yet another embodiment of the compound of formula I, $R_1$ is a side chain of a natural amino acid; $R_7$ is absent; X is

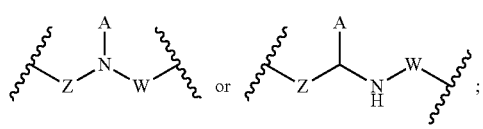

Y is 1,2,3-triazolyl; and $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxy-alkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$ and $^{131}I$. In one variation, Z is

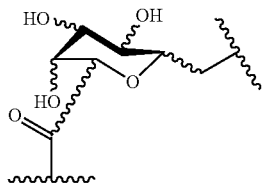

and A is

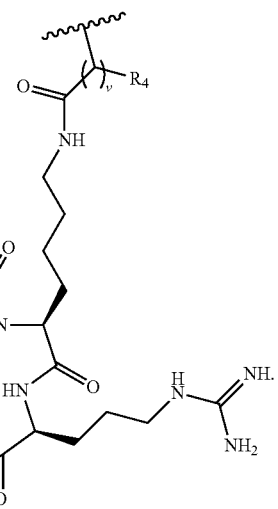

In yet another variation, Z is

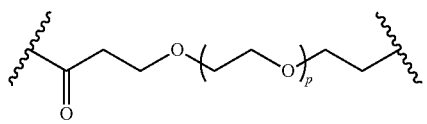

and A is

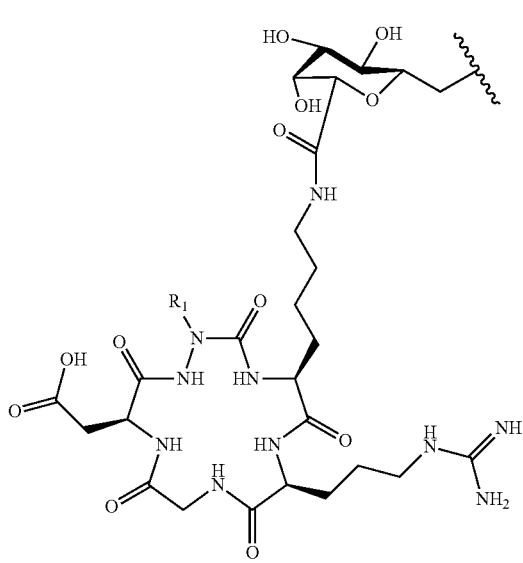

In another variation, Z is

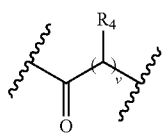

One aspect of the present application is a cycloazapeptide of formula II:

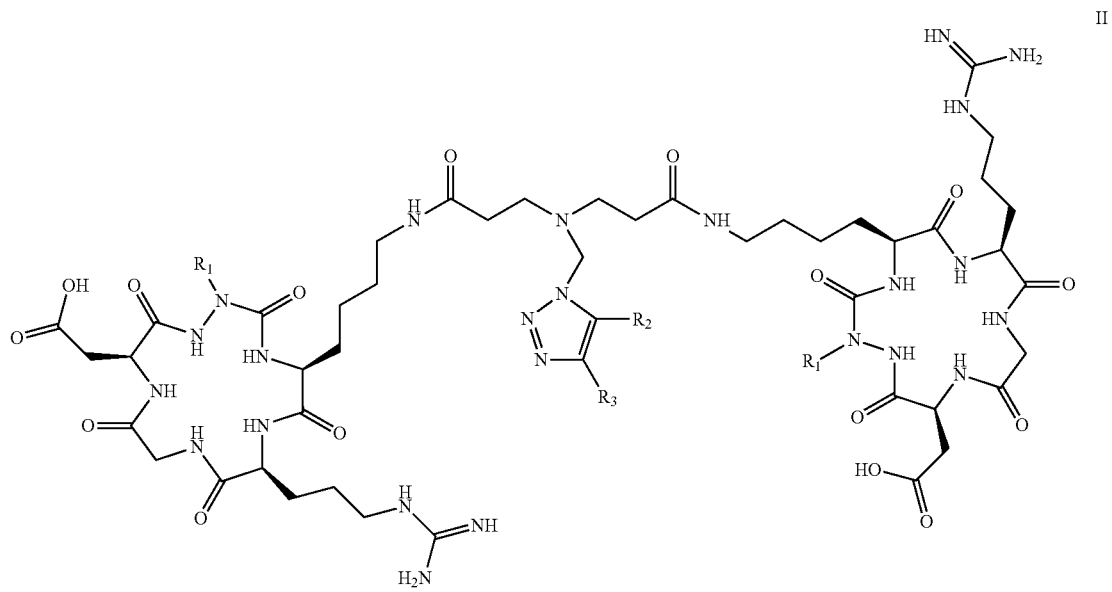

wherein each $R_1$ is hydrogen or is independently selected from the group consisting of a side chain of a natural amino acid and a side chain of an unnatural amino acid;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$ and $^{131}I$;

W is

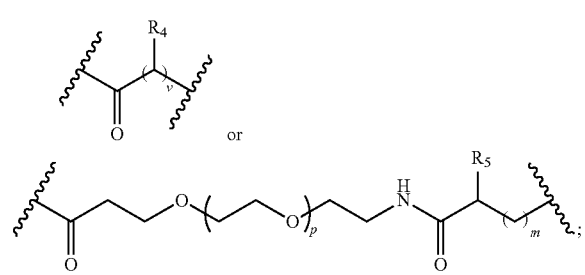

where p is an integer between 0 and 15; v is 0, 1, 2, or 3; m is 0, 1 or 2; each $R_4$ is independently selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted; $R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted; and wherein the configuration of the chiral center that is substituted with the $R_5$ substituent may be R or S or mixtures thereof.

In yet another embodiment, W is

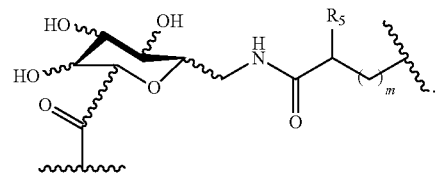

In one embodiment of the any of the disclosed aspects, each $R_1$ is benzyl; $R_2$ is H; $R_3$ is an optionally substituted $C_1$-$C_6$ alkyl comprising a radionuclide selected from the group consisting of $^{11}C$, $^{13}N$, $^{15}O$, $^{18}F$, $^{75}Br$, $^{124}I$, $^{125}I$ and $^{131}I$; and W is

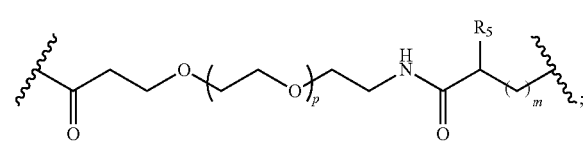

where p is 0, 1, 2, 3, 4 or 5.

Another aspect of the present application is a cycloazapeptide of formula III:

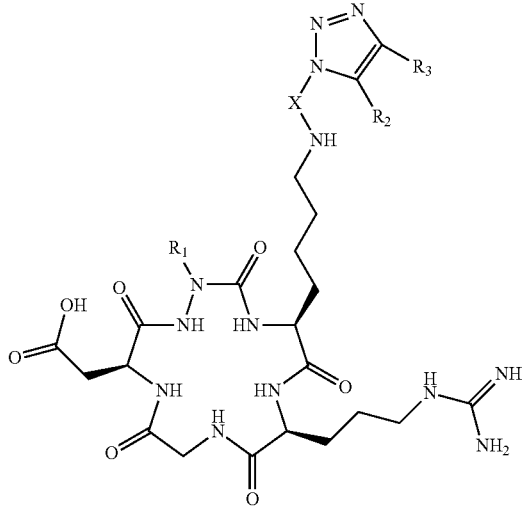

wherein $R_1$ is hydrogen or is selected from the group consisting of a side chain of a natural amino acid and a side chain of an unnatural amino acid; $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted; wherein $R_2$ and $R_3$ are not both H; and either $R_2$ or $R_3$, or both $R_2$ and $R_3$ comprise a radionuclide selected from the group consisting of positron or gamma emitters; and X is a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic and sugar moiety, or a combination thereof.

In one variation any of the embodiments and aspects disclosed herein, $R_1$ is a side chain of a natural amino acid; $R_2$ is hydrogen; and $R_3$ comprises a radionuclide selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$. In another variation, $R_1$ is benzyl; and $R_3$ comprises a radionuclide selected from the group consisting of $^{11}C$, $^{13}N$, $^{15}O$, $^{18}F$, $^{124}I$, $^{125}I$, $^{131}I$, and $^{75}Br$. In yet another embodiment, $R_1$ is a side chain of a natural amino acid; X is selected from the group consisting of:

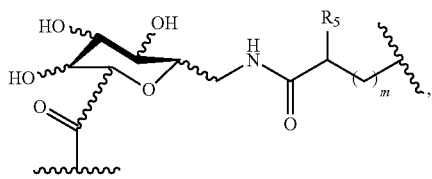

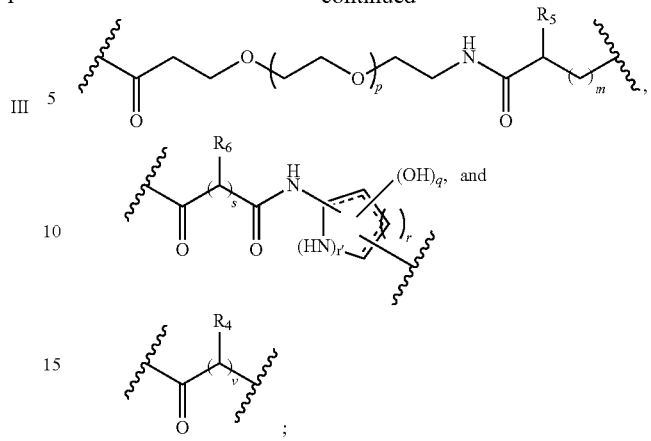

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, aryl, carbocycle and heterocycle groups are each optionally substituted;

each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl and $C_1$-$C_6$-alkoxy-$C_1$-$C_6$-alkyl, wherein the alkyl, alkenyl, alkynyl, alkyloxy and aryl-alkylene groups are each optionally substituted;

v is 0, 1, 2, 3, or 4; m is 0, 1, 2, 3 or 4; p is an integer between 1 and 110; q is 1, 2, 3 or 4; r is 1, 2 or 3; r' is 0 or 1; s is 1, 2, 3 or 4; and the radionuclide is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$; where the configuration of the chiral centers may be R or S or mixtures thereof.

In another embodiment, $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$ and $^{131}I$; X is

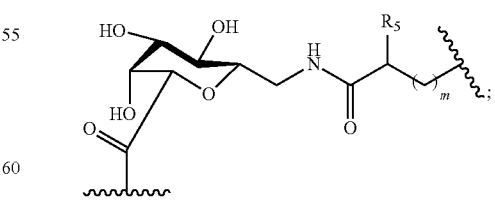

where $R_5$ is selected from the group consisting of —H, $C_1$-$C_6$ alkyl, $C_2$-$C_6$ alkenyl and $C_2$-$C_6$ alkynyl, wherein the alkyl, alkenyl and alkynyl groups are each optionally substituted and wherein the configuration of the chiral center that is substituted with the $R_5$ substituent may be R or S or mixtures thereof; and m is 0, 1 or 2.

In yet another embodiment, $R_2$ is hydrogen; $R_3$ is selected from the group consisting of $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, alkoxyalkyl, aryl, carbocycle and heterocycle, groups are each optionally substituted; wherein $R_3$ comprises a radionuclide selected from the group consisting of $^{11}C$, $^{13}N$, $^{15}O$, and $^{18}F$; $R_5$ is hydrogen; and m is 0.

In a further embodiment, $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, alkoxyalkyl, aryl, carbocycle and heterocycle, groups are each optionally substituted; wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$, and $^{131}I$;

X is

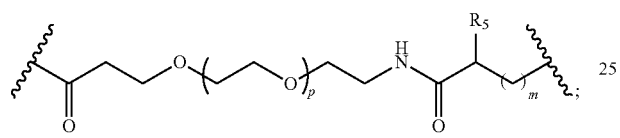

where $R_5$ is selected from the group consisting of —H, $C_1$-$C_6$ alkyl, $C_2$-$C_6$ alkenyl and $C_2$-$C_6$ alkynyl, wherein the alkyl, alkenyl and alkynyl groups are each optionally substituted and wherein the configuration of the chiral center that is substituted with the $R_5$ substituent may be R or S or mixtures thereof; m is 0, 1, or 2; and p is an integer between 1 and 90.

In still another embodiment, $R_2$ is hydrogen; $R_3$ is selected from the group consisting of $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted, and $R_3$ comprises a radionuclide selected from the group consisting of $^{11}C$, $^{13}N$, $^{15}O$, and $^{18}F$; $R_5$ is hydrogen; m is 0; and p is an integer between 1 and 15.

In another embodiment of any of the aspects disclosed herein, X is

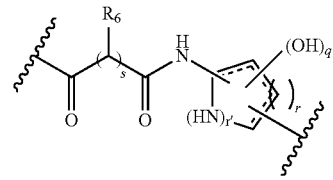

where each $R_6$ is independently selected from the group consisting of —H, —OH, $C_1$-$C_6$ alkyl, $C_2$-$C_6$ alkenyl, $C_1$-$C_6$ alkyloxy, hydroxy-$C_1$-$C_6$-alkyl, and $C_1$-$C_6$-alkoxy-$C_1$-$C_6$-alkyl, wherein the alkyl, alkenyl and alkyloxy groups are each optionally substituted; q is 2, 3 or 4; r is 2 or 3; r' is 0; and s is 1 or 2.

In yet another embodiment of the present application, X is

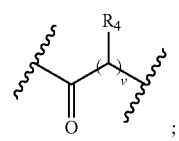

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, hydroxy-$C_1$-$C_6$-alkyl, $C_1$-$C_6$-alkoxy-$C_1$-$C_6$-alkyl and a PEG moiety, wherein the alkyl, alkenyl, alkynyl, alkoxy, aryl, carbocycle and heterocycle groups are each optionally substituted; and v is 1, 2, 3, or 4. In one variation, each $R_4$ is independently selected from the group consisting of —H, $C_1$-$C_6$ alkyl, $C_2$-$C_6$ alkenyl, $C_2$-$C_6$ alkynyl and a PEG moiety, wherein the alkyl, alkenyl and alkynyl groups are each optionally substituted.

One aspect of the present application is a radiolabeled cycloazapeptide of formula IV:

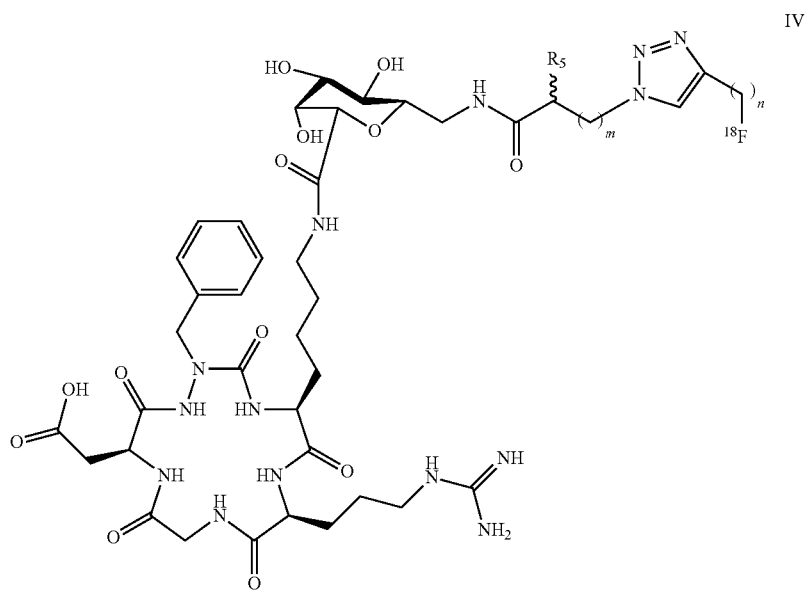

wherein: $R_5$ is selected from the group consisting of H, $C_1$-$C_6$ alkyl, $C_2$-$C_6$ alkenyl, $C_2$-$C_6$ alkynyl, $C_1$-$C_6$ alkyloxy, aryl, —($C_1$-$C_6$ alkylene)-aryl, 3- to 7-membered carbocycle, 3- to 7-membered heterocycle, hydroxy-$C_1$-$C_6$-alkyl, and $C_1$-$C_6$-alkoxy-$C_1$-$C_6$-alkyl; wherein the alkyl, alkenyl, alkynyl, alkyloxy, aryl, carbocycle and heterocycle groups are each optionally substituted; wherein the chiral centers attached to ∿ bonds are R or S or mixtures thereof; m is 0, 1, 2, 3 or 4; and n is 1, 2, 3, 4 or 5.

In one embodiment, $R_5$ is selected from the group consisting of H, $C_1$-$C_4$ alkyl, $C_2$-$C_4$ alkenyl, and $C_2$-$C_4$ alkynyl, wherein the alkyl, alkenyl and alkynyl groups are each optionally substituted; wherein the chiral center in the cyclic peptide is R configured and the chiral center bearing the $R_5$ residue is R or S or mixtures thereof; m is 0, 1 or 2; and n is 1, 2, 3 or 4. In another embodiment, $R_5$ is selected from the group consisting of —H, and an optionally substituted $C_1$-$C_4$ alkyl; m is 0 or 1; and n is 2, 3 or 4.

Another aspect of the present application is a radiolabeled cycloazapeptide selected from the group consisting of:

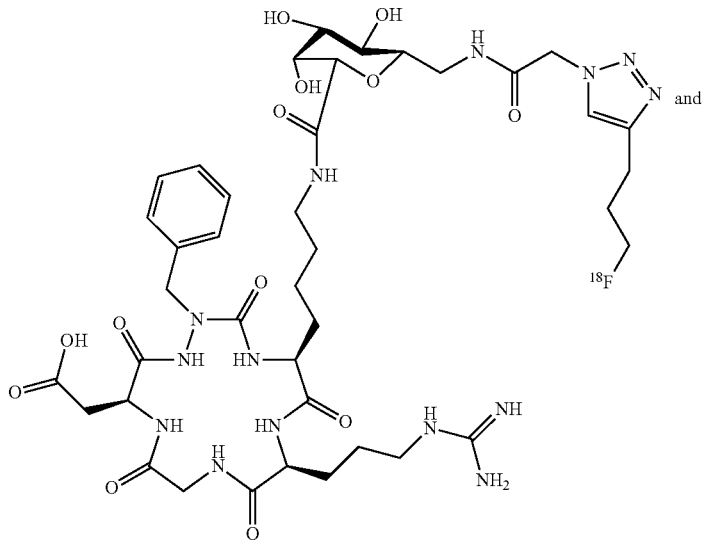

and

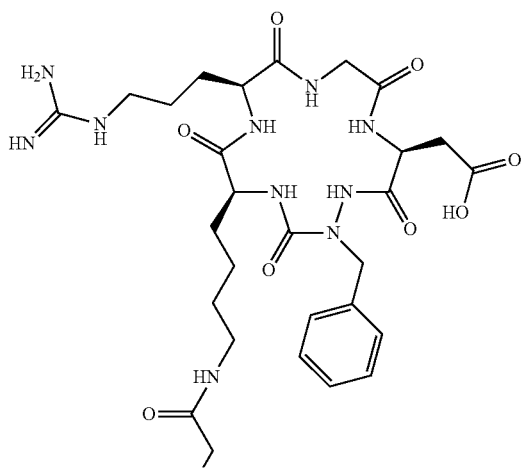

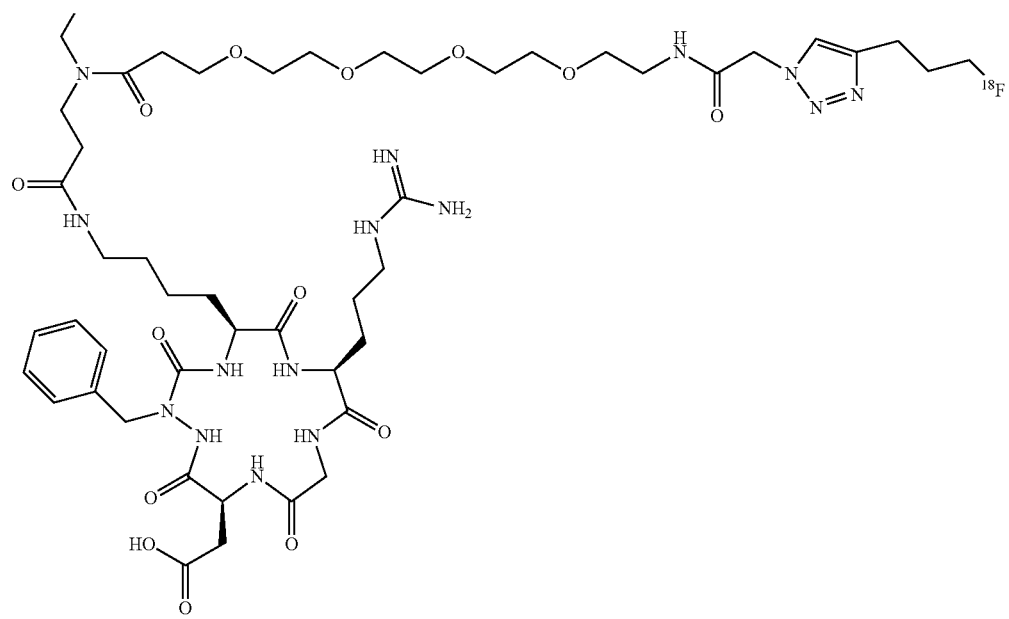
Yet another aspect of the present application is a pharmaceutical composition comprising a radiolabeled cycloazapeptide of the formula I, formula II and formula II as defined herein.
Still another aspect of the present application is a pharmaceutical composition comprising a radiolabeled cycloazapeptide selected from the group consisting of:
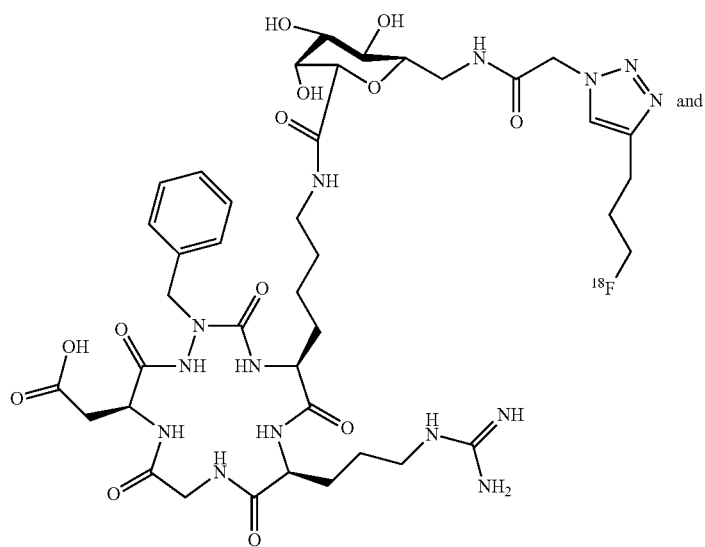
and -continued

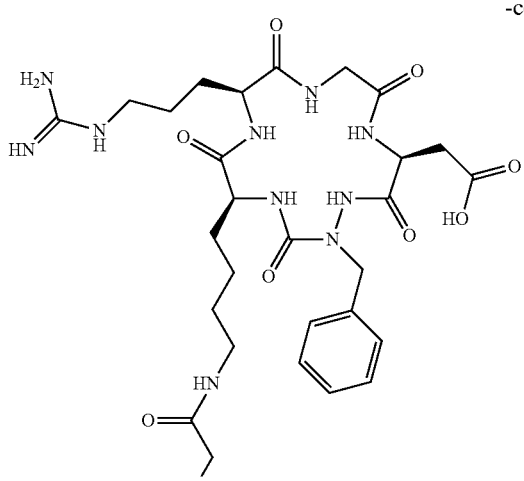

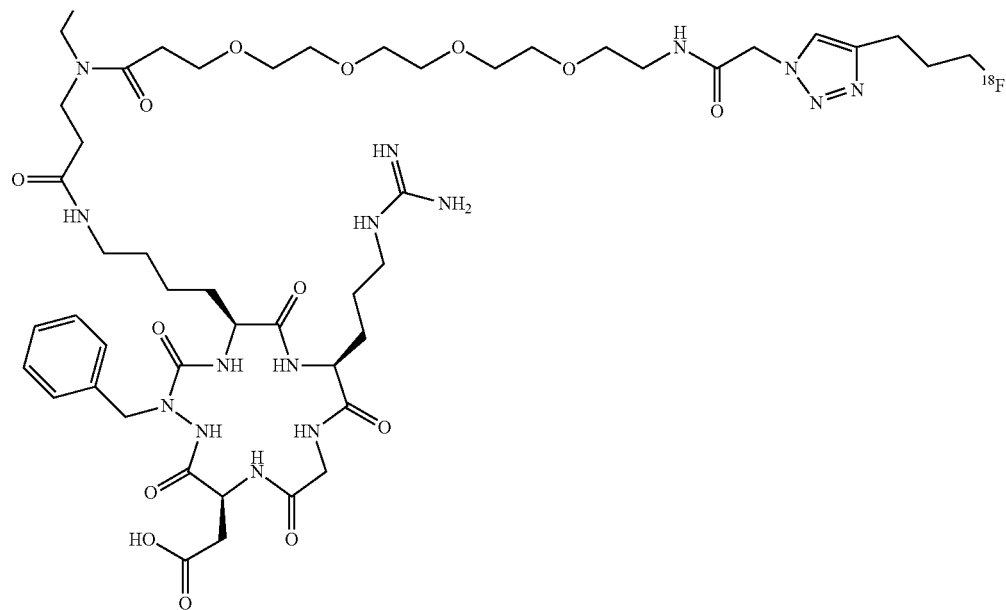

and a pharmaceutically acceptable carrier.

One aspect of the present application is a method of monitoring the level of integrin $\alpha_v\beta_3$ or visualizing integrin $\alpha_v\beta_3$ expression within a body of a patient, the method comprising: (a) administering to the patient a radiolabeled cycloazapeptide; and (b) employing a nuclear imaging technique selected from the group consisting of positron emission tomography (PET) and single photon emission computed tomography (SPECT) for monitoring or visualizing a distribution of the radiolabeled cycloazapeptide within the body or within a portion thereof; wherein the radiolabeled cycloazapeptide is of formula I, as defined herein.

Another aspect of the present application is a method of monitoring the level of integrin $\alpha_v\beta_3$ or visualizing integrin $\alpha_v\beta_3$ expression within a body of a patient, the method comprising: (a) administering to the patient a radiolabeled cycloazapeptide; and (b) employing a nuclear imaging technique selected from the group consisting of positron emission tomography (PET) and single photon emission computed tomography (SPECT) for monitoring or visualizing a distribution of the radiolabeled cycloazapeptide within the body or within a portion thereof; wherein the radiolabeled cycloazapeptide is of formula II or formula III:

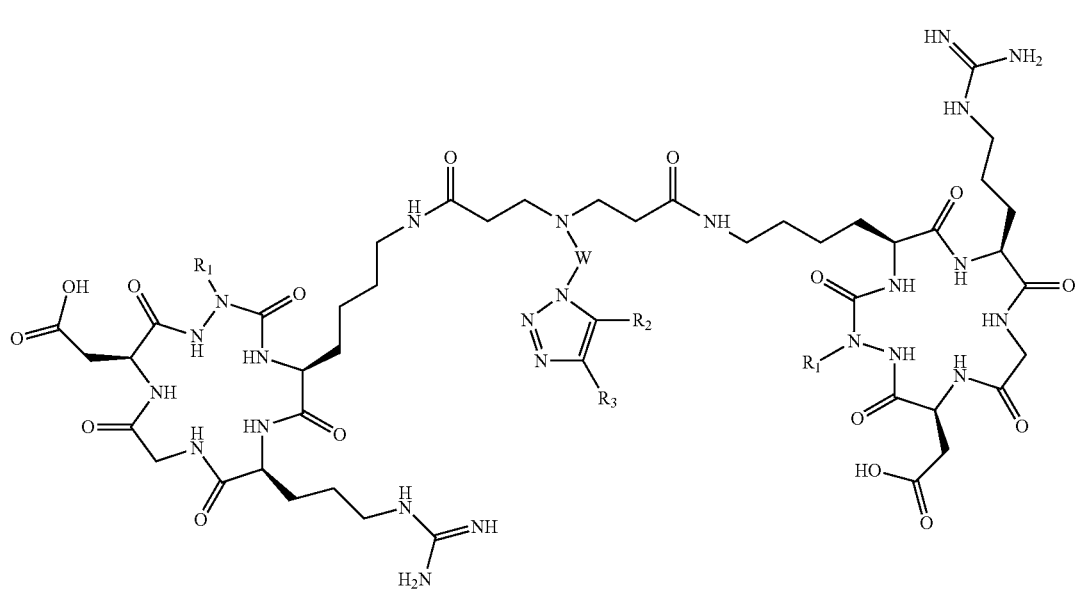

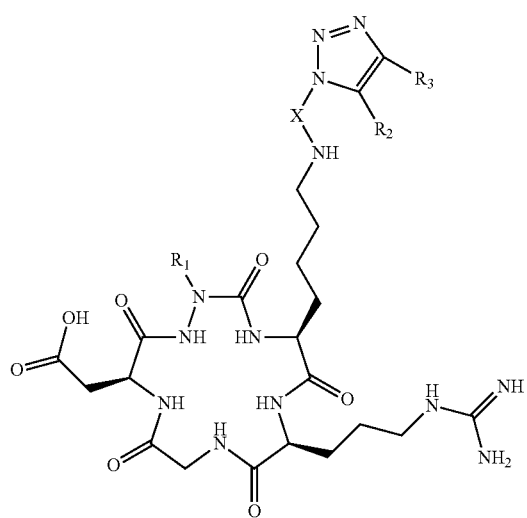

wherein each $R_1$ is independently selected from the group consisting of a side chain of a natural amino acid and a side chain of an unnatural amino acid;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, alkoxyalkyl, aryl, carbocycle and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{61}$Cu, $^{62}$Cu, $^{64}$Cu, $^{67}$Cu, $^{68}$, $^{124}$I, $^{125}$I, $^{131}$I, $^{99}$Tc, $^{75}$Br, $^{153}$Gd and $^{32}$P;

each of X and W is selected from the group consisting of:

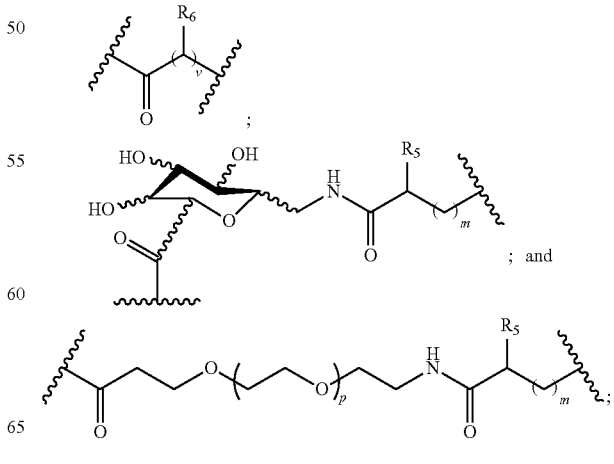

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted; wherein the configuration of the chiral centers may be R or S or mixtures thereof; v is 0, 1, 2, 3, or 4; m is 0, 1, 2, 3 or 4; and p is an integer between 1 and 25.

Yet another aspect of the present application is a method of monitoring the level of integrin $\alpha_v\beta_3$ or visualizing integrin $\alpha_v\beta_3$ expression within a body of a patient, the method comprising: (a) administering to the patient a radiolabeled cycloazapeptide; and (b) employing a nuclear imaging technique selected from the group consisting of positron emission tomography (PET) and single photon emission computed tomography (SPECT) for monitoring or visualizing a distribution of the radiolabeled cycloazapeptide within the body or within a portion thereof; wherein the radiolabeled cycloazapeptide is selected from the group consisting of:

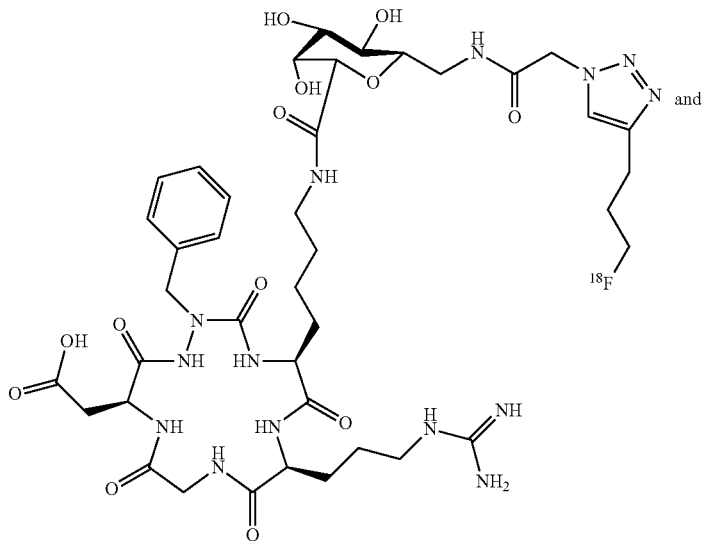

and

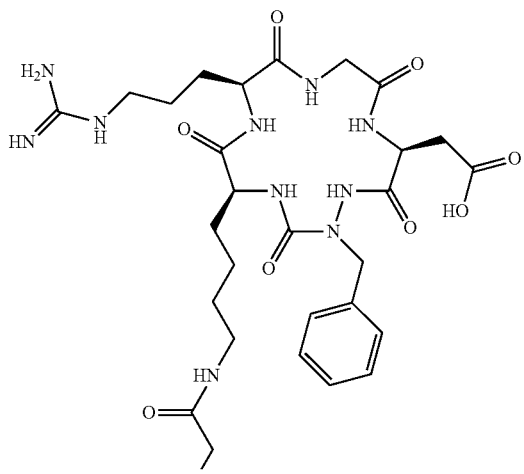

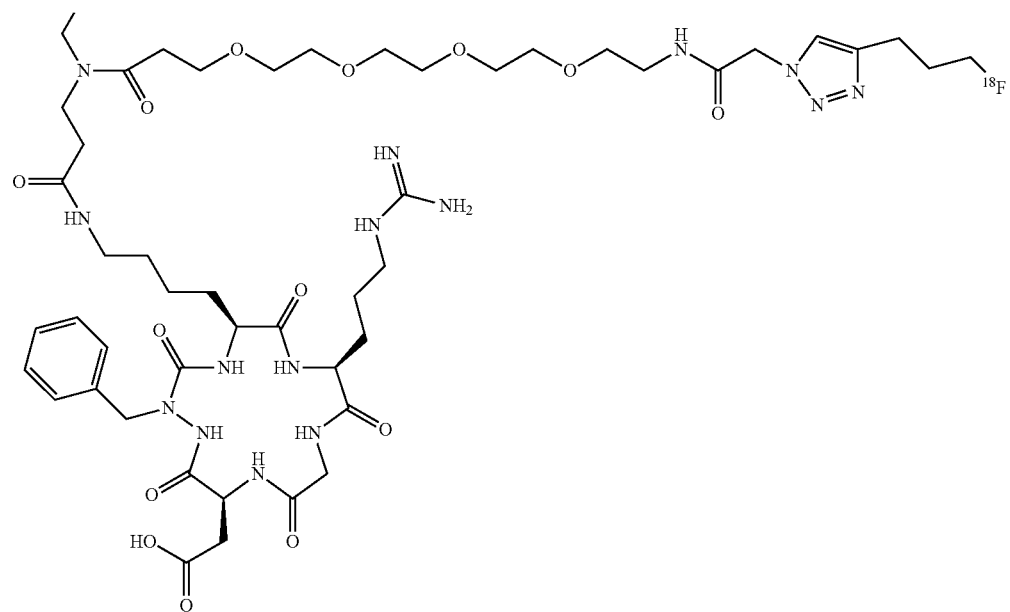
Yet another aspect of the present application is a cyclic azapeptide selected from the group consisting of:
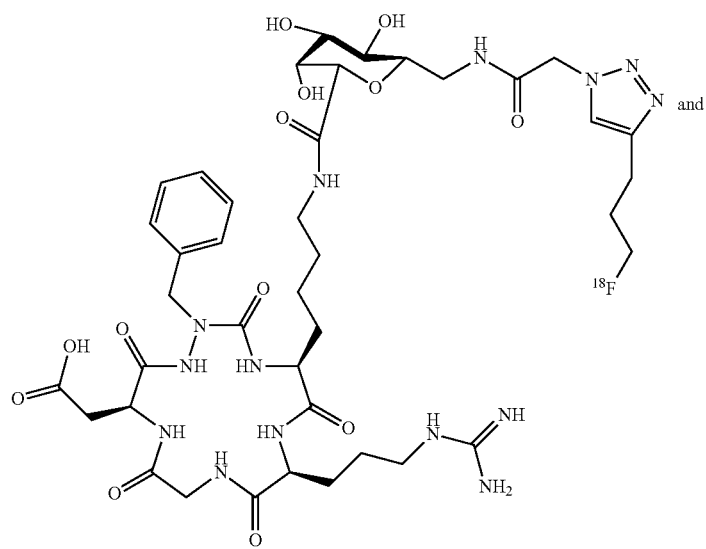
and -continued

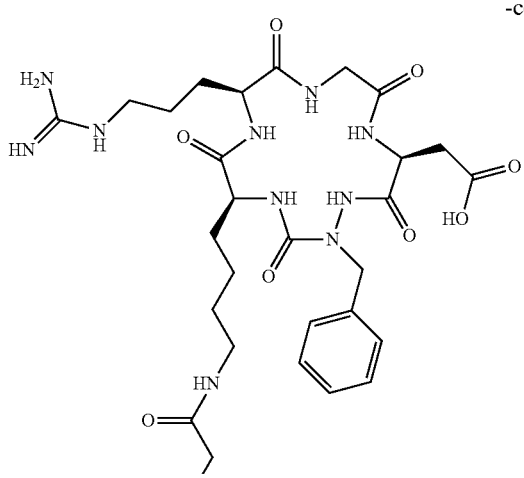

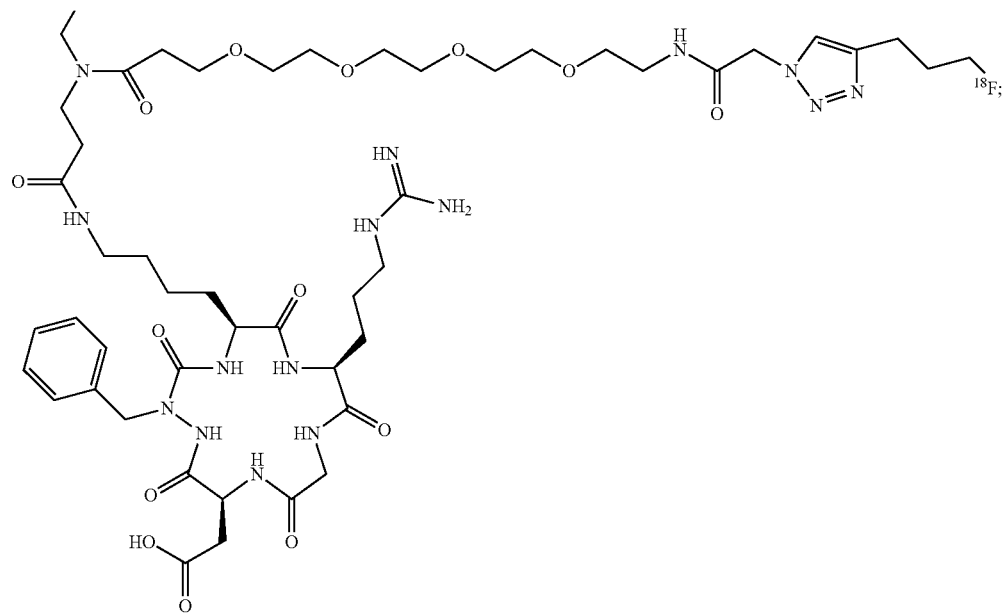

and a pharmaceutically acceptable carrier.

A still further aspect of the present application is a method for imaging of blood vessel growth in solid tumors based on expression of integrin $\alpha_v\beta_3$ within the body of a patient, the method comprising: (a) administering to the patient a radiolabeled cycloazapeptide; (b) employing a nuclear imaging technique selected from the group consisting of positron emission tomography (PET) and single photon emission computed tomography (SPECT) for imaging a distribution of the radiolabeled cycloazapeptide within the body or within a portion thereof; and c) correlating the distribution of the radiolabeled cycloazapeptide to the growth of blood vessels in solid tumors, wherein the radiolabeled cycloazapeptide is of formula I as defined herein.

Yet another aspect of the present application is a method for imaging of blood vessel growth in solid tumors based on expression of integrin $\alpha_v\beta_3$ within the body of a patient, the method comprising: (a) administering to the patient a radiolabeled cycloazapeptide; (b) employing a nuclear imaging technique selected from the group consisting of positron emission tomography (PET) and single photon emission computed tomography (SPECT) for imaging a distribution of the radiolabeled cycloazapeptide within the body or within a portion thereof; and c) correlating the distribution of the radiolabeled cycloazapeptide to the growth of blood vessels in solid tumors, wherein the radiolabeled cycloazapeptide is of formula II or formula III as defined herein.

Yet another aspect of the present application is a method for imaging of blood vessel growth in solid tumors based on expression of integrin $\alpha_v\beta_3$ within the body of a patient, the method comprising: (a) administering to the patient a radiolabeled cycloazapeptide; (b) employing a nuclear imaging technique selected from the group consisting of positron emission tomography (PET) and single photon emission computed tomography (SPECT) for imaging a distribution of the radiolabeled cycloazapeptide within the body or within a portion thereof; and c) correlating the distribution of the radiolabeled cycloazapeptide to the growth of blood vessels in solid tumors, wherein the radiolabeled cycloazapeptide is selected from the group consisting of:

41 42
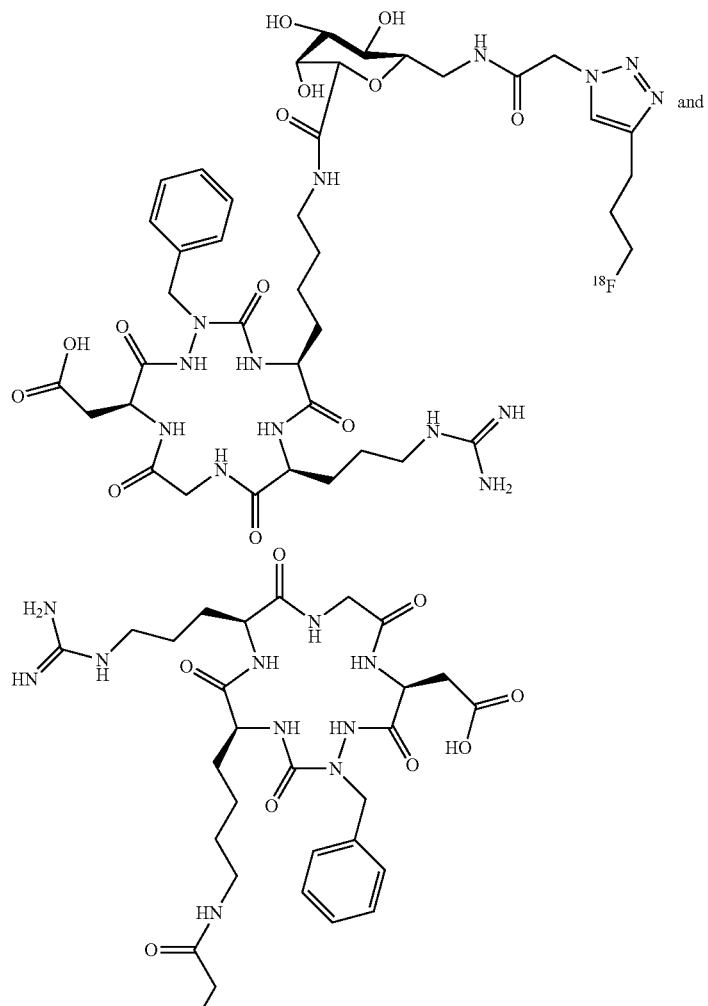
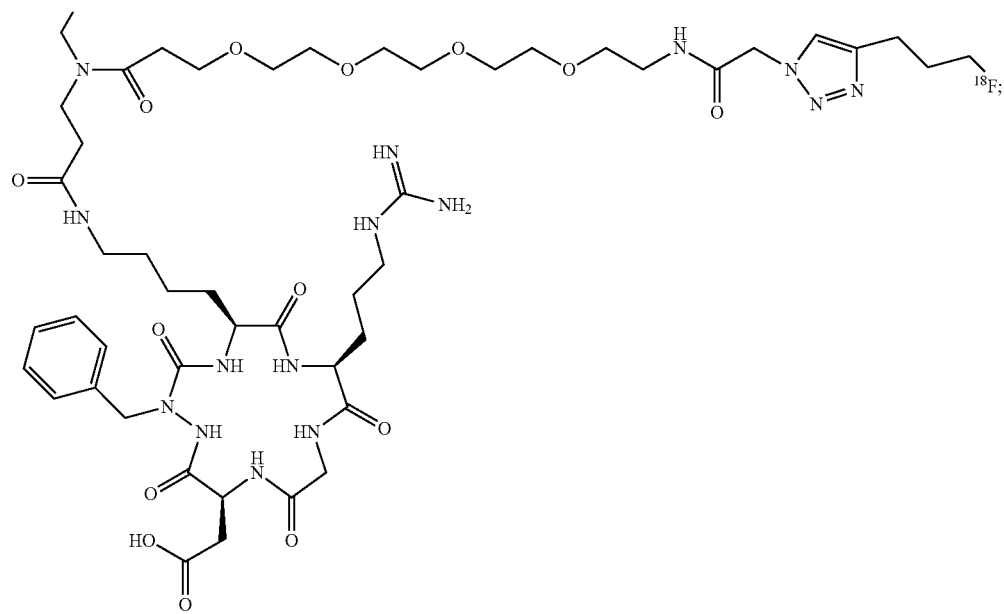

One aspect of the present invention is a compound of formula V:

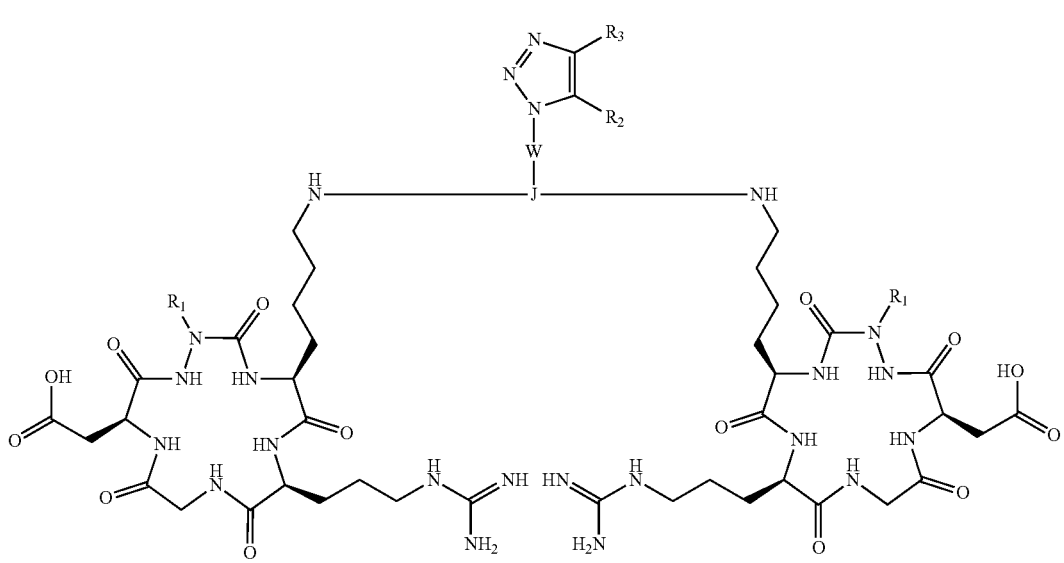

V wherein each $R_1$ is independently selected from the group consisting of a side chain of a natural amino acid and a side chain of an unnatural amino acid; $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted; wherein $R_2$ and $R_3$ are not both H; and either $R_2$ or $R_3$, or both $R_2$ and $R_3$ comprise a radionuclide selected from the group consisting of positron or gamma emitters; W is a linker comprising zero, one or more moieties selected from the group consisting of hydroxyl, carbonyl, sulfonamide, sulfonate, phosphate, polar amino acid moiety, PEG moiety, sugar mimetic, and a sugar moiety; J is a linker comprising a moiety selected from the group consisting of $C_1$-$C_6$ alkyl, —$C_1$-$C_6$ alkenyl, —$C_1$-$C_6$ alkynyl, aryl, aryl-($C_1$-$C_6$ alkylene)-, 3- to 7-membered carbocycle, 3- to 7-membered heterocycle, and natural amino acids wherein the alkyl, alkenyl, alkynyl, aryl, carbocycle and heterocycle groups are each optionally substituted. In one aspect, the radionuclide is selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P; W is selected from the group consisting of where $R_4$ is independently —H, —$C_1$-$C_6$ alkyl, $C_1$-$C_6$ alkenyl, $C_1$-$C_6$ alkynyl, $C_1$-$C_6$ alkyloxy, aryl, aryl-($C_1$-$C_6$ alkylene)-, $C_3$-$C_7$ carbocycle, 3- to 7-membered heterocycle, hydroxy-$C_1$-$C_6$-alkyl, $C_1$-$C_6$-alkoxy-$C_1$-$C_6$-alkyl and a PEG moiety, $R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, aryl, carbocycle and heterocycle groups are each optionally substituted; each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl and $C_1$-$C_6$-alkoxy-$C_1$-$C_6$-alkyl, wherein the alkyl, alkenyl, alkynyl, alkyloxy and aryl-alkylene groups are each optionally substituted; p is an integer between 0 and 15; q is 1, 2, 3 or 4; r is 1, 2 or 3; r' is 0 or 1; s is 1, 2, 3 or 4; and m is 0, 1, 2, 3, 4 or 5; wherein the configuration of any of the chiral centers may optionally be R or S. In another embodiment, J is

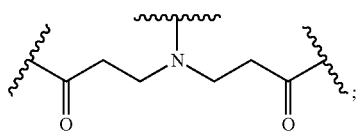 [SMILES: *C(=O)CCN(*)CCC(*)=O]
and the radionuclide is selected from the group consisting of $^{11}C$, $^{13}N$, $^{15}O$, $^{18}F$, $^{124}I$, $^{125}I$, $^{131}I$, and $^{75}Br$. In yet another embodiment, J is
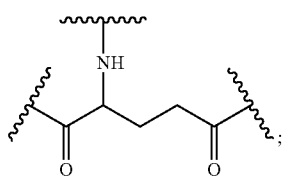 [SMILES: *NC(CCC(*)=O)C(*)=O]
and the radionuclide is selected from the group consisting of $^{11}C$, $^{13}N$, $^{15}O$, $^{18}F$, $^{124}I$, $^{125}I$, $^{131}I$, and $^{75}Br$.
One aspect of the present invention is a compound of formula VI:
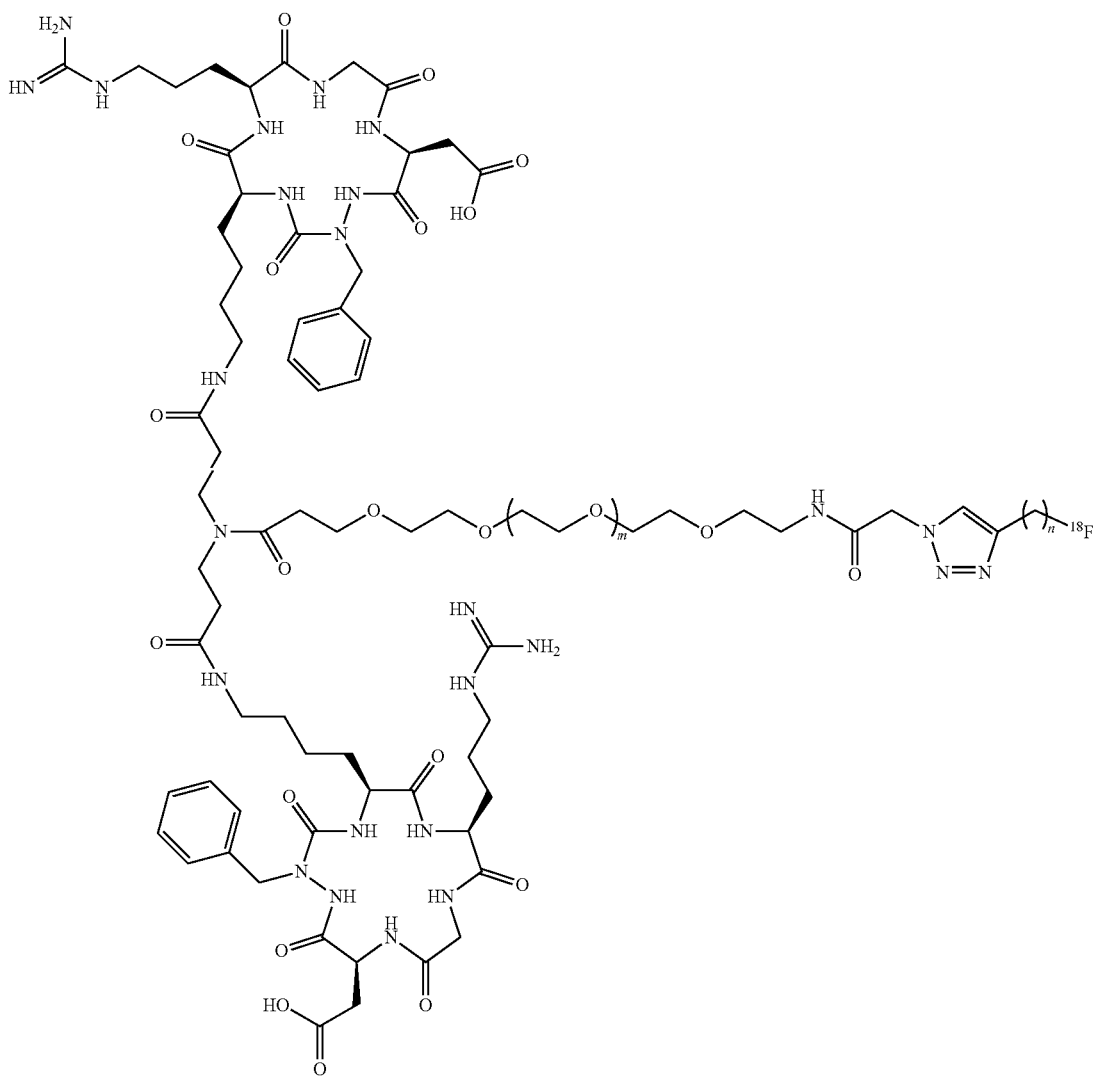
m is 0 to 4, and n is 1-5. In one variation, m is 0 and n is 3.

In another aspect, there is provided a pharmaceutical composition comprising any of the above disclosed compounds and a pharmaceutically acceptable carrier. In yet another aspect of the present application, the compounds disclosed herein may be used as tracers in Positron Emission Tomography (PET) or Single Photon Emission Computed Tomography (SPECT).

In another embodiment, there is provided a method of monitoring the level of integrin receptor within a body of a patient, the method comprising: (a) administering to the patient any of the above cited radiolabeled cycloazapeptides, and (b) employing a nuclear imaging technique selected from the group consisting of positron emission tomography (PET) and single photon emission computed tomography (SPECT) for monitoring a distribution of the cyclic polypeptide within the body or within a portion thereof. In one embodiment, the integrin receptor is $\alpha_v\beta_3$.

Another aspect of the present application is a method of visualizing integrin expression within a body of a patient, the method comprising: (a) administering to the patient any of the above cited radiolabeled cycloazapeptides; and (b) employing a nuclear imaging technique selected from the group consisting of positron emission tomography (PET) and single photon emission computed tomography (SPECT) for visualizing a distribution of the radiolabeled cycloazapeptide within the body or within a portion thereof. In one embodiment, the integrin receptor is $\alpha_v\beta_3$.

Another aspect of the present application is a method for imaging of blood vessel growth in solid tumors based on expression of integrin $\alpha_v\beta_3$ within the body of a patient, the method comprising: (a) administering to the patient any of the above cited the radiolabeled cycloazapeptides; (b) employing a nuclear imaging technique selected from the group consisting of positron emission tomography (PET) and single photon emission computed tomography (SPECT) for imaging a distribution of the radiolabeled cycloazapeptide within the body or within a portion thereof; and c) correlating the distribution of the radiolabeled cycloazapeptide to the growth of blood vessels in solid tumors. In one embodiment, the integrin receptor is $\alpha_v\beta_3$.

The integrin $\alpha_v\beta_3$ plays an important role in regulating tumor growth and angiogenesis. The non-invasive visualization and quantification of $\alpha_v\beta_3$ integrin levels in patients enables a variety of applications. One such application is determination of $\alpha_v\beta_3$ levels before therapy with $\alpha_v\beta_3$ antagonists. Patients with low or no $\alpha_v\beta_3$ expression might not benefit from $\alpha_v\beta_3$ antagonist therapy and could then receive alternate treatment. Patients with $\alpha_v\beta_3$ positive lesions could have their treatment optimized, based on the use of the compounds of the present application to evaluate inhibition of the $\alpha_v\beta_3$ integrin.

In one embodiment, there is provided a method for selectively binding integrin receptors in a mammal, the method comprising administering a therapeutically effective amount of a cyclic azapeptide as provided herein, or a pharmaceutical composition thereof. In one aspect, the binding of integrin receptors is effective for reducing, minimizing or substantially eliminating tumor progression.

Pharmaceutical compositions of the compounds of this application, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic aqueous solution. Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidinone, gelatin, hydroxycellulose, acacia, polyethylene glycol, mannitol, sodium chloride or sodium citrate, may also be added. Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols or water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax. The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation may be in the form of a syrup, elixir, emulsion, or an aqueous or non-aqueous suspension. Such a liquid formulation may be administered directly p.o. or filled into a soft gelatin capsule. Suitable formulations for each of these methods of administration may be found in, for example, REMINGTON: THE SCIENCE AND PRACTICE OF PHARMACY, A. Gennaro, ed., 20th edition, Lippincott, Williams & Wilkins, Philadelphia, Pa.

The pharmaceutical compositions of the application may be in the form of a sterile injectable preparation. Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents.

The following procedures may be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Certain "protective groups" such as an N-acetyl group, may be incorporated and remain as part of the desired compound. Suitable protective groups for amino, hydroxy and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989.

Radio-labeling a small molecule, such as a compound of the present application, usually involves displacement of a suitably activated precursor with a radioactive moiety in a compatible reaction media. In the case of $^{18}$F-labeling, the [$^{18}$F] fluoride attachment to the precursor occurs via nucleophilic substitution of a leaving group, such as mesylate, tosylate, bromide, iodide or diazonium salt, or nitro group. Depending on the compound, the preparation of a radio-labeled compound generally consists of at least two steps. The first step involves the preparation of radio-labeling precursor, in which various functional groups have been appropriately protected and a proper leaving group has been incorporated. The second sequence then involves the radio-labeling, and removal of the protecting group as known in the art.

EXAMPLES

The novel cycloazapeptide compounds disclosed in this application are prepared using click chemistry [9-17]. Click chemistry, as used in this application, describes the rapid, selective and specific formation of 1,4- or 1,5-disubstituted 1,2,3-triazoles starting from alkyl azides and terminal alkynes. One or more triazole moieties are attached to the cyclic peptide, the hydrophilic linker, or the radiolabel tag. Click chemistry is a high-yielding and modular approach and as such, the pharmacokinetic properties of these cycloazapeptide analogs are easily modified.

Scheme I provides an exemplary reaction scheme for the synthesis of a cycloazapeptide containing Arg-Gly-Asp (RGD) fragment.

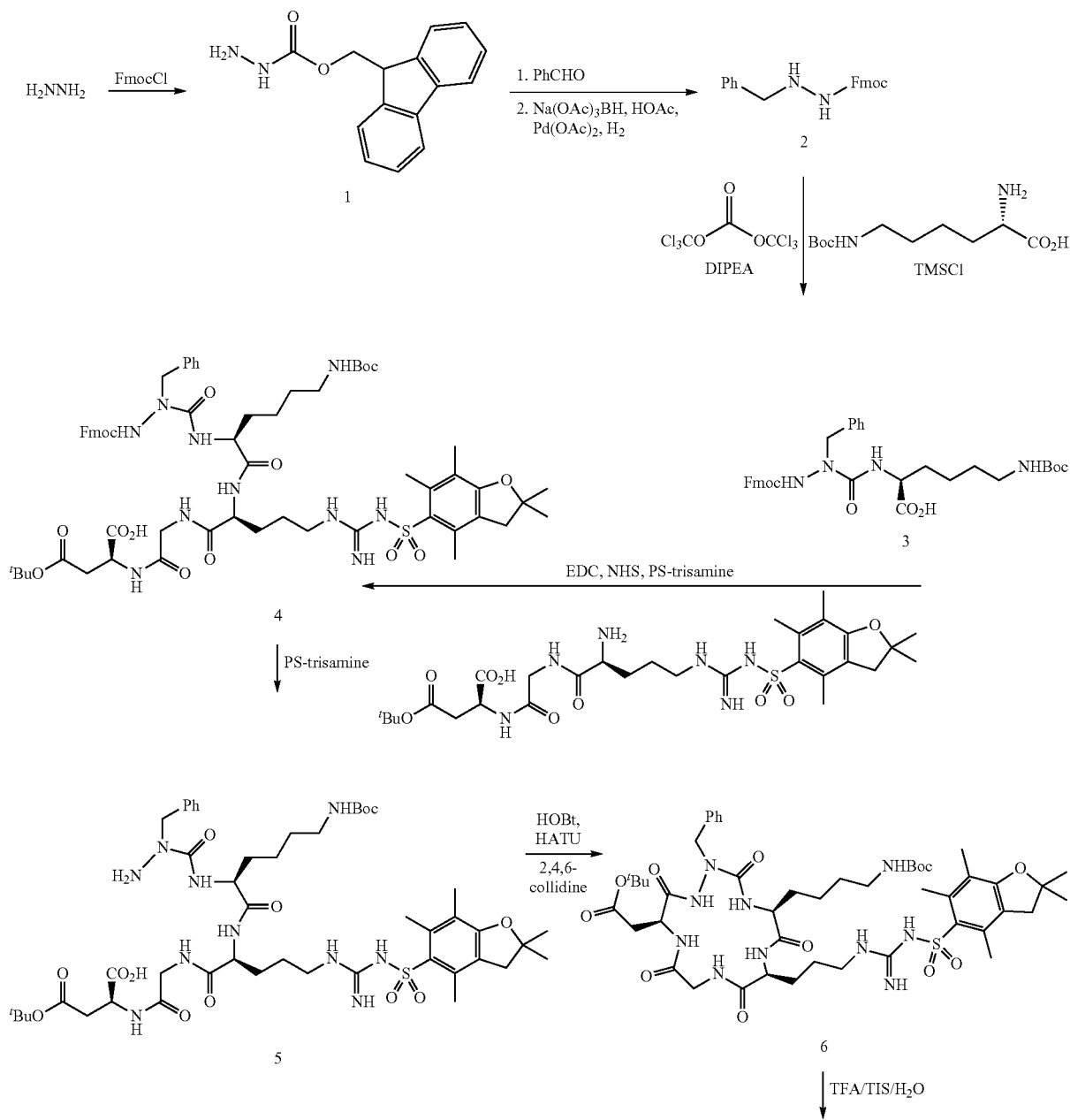

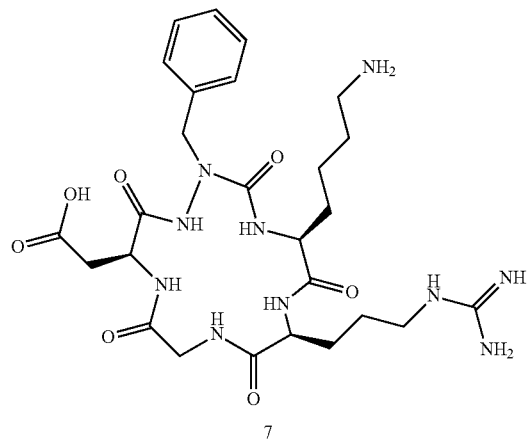

7

Synthesis of Compound 7

Synthesis of (9H-fluoren-9-yl)methyl hydrazinecarboxylate (Compound 1)

To a round bottom flask containing hydrazine (9.3 g, 0.291 mol) in diethyl ether (anhydrous, 200 mL) at ice bath temperature, was added 9-fluorenylmethyl chloroformate (25 g, 97 mmol) in diethyl ether (anhydrous, 200 mL) dropwise in a two-hour time period. After addition, the reaction was allowed to room temperature and stirred overnight. The reaction was concentrated in vacuo to remove the volatiles. The white solid residue was washed with water (500 mL), filtered and dried to afford compound 1 (24.2 g, 95 mmol, 99% yield). $^1$H NMR (400 MHz, $d_6$-DMSO) δ: 8.34 (br, 1H), 7.88 (m, 2H), 7.73 (m, 2H), 7.42-7.25 (m, 4H), 4.30-4.20 (m, 3H), 4.05 (br, 2H).

Synthesis of (9H-fluoren-9-yl)methyl 2-benzylhydrazinecarboxylate (Compound 2)

To a round bottom flask containing compound 1 (24 g, 95 mmol) suspended in MeOH (250 mL) and THF (250 mL), was added benzylaldehyde (10 g, 94 mmol) dropwise. The suspension turned into a yellow clear solution. After stirred at room temperature for an hour, the reaction mixture was concentrated to 100 mL in vacuo. White precipitate was filtered. The filtrate was concentrated again (to 30 mL) and filtered again. The combined crude product was filtered again to afford a white solid (25 g, 74 mmol, 78% yield) as the imine intermediate. To a round bottom flask containing imine intermediate (19 g, 56 mmol) in THF (350 mL) was added acetic acid (5.0 g, 83 mmol), Na(OAc)$_3$BH (18 g, 83 mmol). The mixture was stirred at room temperature for 15 min; palladium acetate (1.9 g, 8.5 mmol) was added. The reaction mixture was stirred at room temperature under hydrogen atmosphere for 30 min. The solution was filtered through a celite plug, concentrated, diluted with NaHCO$_3$ (aqueous, 100 mL) and extracted with EtOAc (200 mL×3). The combined organic layers were dried, concentrated and washed with hexanes (80 mL) via 30 min of sonication. An off-white solid, compound 2 (10.5 g, 30 mmol, 54% yield) was isolated via filtration and drying in vacuo overnight. $^1$H NMR (400 MHz, $d_6$-DMSO) δ: 8.71 (br, 1H), 7.89 (m, 2H), 7.68 (m, 2H), 7.42-7.35 (m, 2H), 7.31-7.22 (m, 6H), 4.95 (br, 1H), 4.32-4.20 (m, 3H), 3.88 (s, 2H); LRMS for $C_{22}H_{20}N_2O_2$, calc'd: 344.2. found: 345.2 [M+H]$^+$.

Synthesis of (S)-5-benzyl-1-(9H-fluoren-9-yl)-16,16-dimethyl-3,6,14-trioxo-2,15-dioxa-4,5,7,13-tetraazaheptadecane-8-carboxylic acid (Compound 3)

To a round bottom flask containing Boc-protected Lysine (1.7 g, 7.0 mmol) in DCM (18 ml), were added DIPEA (1.3 mL, 7.7 mmol) and chlorotrimethylsilane (0.98 mL, 7.7 mmol). The reaction was stirred at room temperature for 2 h until all precipitate disappeared. To a second round bottom flask containing triphosgen (0.77 g, 2.6 mmol) in DCM (10 mL), was added dropwise a solution of compound 2 (2.5 g, 7.0 mmol), DIPEA (1.3 mL, 7.7 mmol) in DCM (30 mL) during a six-hour period. After the addition, the protected Lysine was added into the second flask in one portion with vigorous stirring. The reaction was stirred at room temperature for 20 min, then diluted with HCl (5% wt, 26 mL). The organic layer was separated. The aqueous layer was extracted with DCM (50 mL×2). The combined organic layers were concentrated and washed with hexanes and ether (4:1, 20 mL). The solid residue was purified on a silica gel plug (MeOH:CHCl$_3$=1:30; then Acetone:MeOH=1:1) to afford compound 3 (1.7 g, 2.8 mmol, 40% yield) as a white solid. $^1$H NMR (400 MHz, $d_6$-DMSO) δ: 9.56 (br, 1H), 7.89 (m, 2H), 7.61 (m, 2H), 7.40-7.10 (m, 9H), 6.67 (br, 1H), 6.50 (br, 1H), 4.38-4.18 (m, 2H), 3.98 (s, 2H), 3.40-3.20 (m, 3H), 2.80 (m, 2H), 1.70-1.50 (m, 2H), 1.31 (s, 9H), 1.20 (m, 2H); LRMS for $C_{34}H_{40}N_4O_7$, calc'd: 616.3. found: 517.3 [M+H−Boc]$^+$.

Synthesis of (8S,11S,17S)-5-benzyl-8-(3-(tert-butoxycarbonylamino)propyl)-1-(9H-fluoren-9-yl)-21,21-dimethyl-3,6,9,12,15,19-hexaoxo-11-(3-(3-(2,2,4,6,7-pentamethyl-2,3-dihydrobenzofuran-5-ylsulfonyl)guanidino)propyl)-2,20-dioxa-4,5,7,10,13,16-hexaazadocosane-17-carboxylic acid (Compound 4)

To a round bottom flask containing compound 3 (630 mg, 1.02 mmol) in DCM (5 ml), were added N-hydroxysuccinimide (115 mg, 1.00 mmol) and EDC (191 mg, 1.00 mmol). After 30 min, a solution of ($^t$BuO)Asp-Gly-Arg(Pbf) (654 mg, 1.00 mmol) in DMF (1.5 mL) was added followed by addition of PS-trisamine (160 mg). The reaction was stirred at room temperature overnight. The reaction was filtered, concentrated and purified on a silica gel column (Acetone:CHCl$_3$:MeOH=35:60:5 followed by Acetone:CHCl$_3$:MeOH=30:40:30) to afford compound 4 (1.2 g, 0.95 mmol, 95% yield). $^1$H NMR (400 MHz, $d_6$-DMSO) δ: 9.58 (br, 1H), 9.50 (br, 1H), 8.40 (br, 1H), 8.20-8.00 (m, 3H), 7.90 (br, 1H), 7.82 (m, 2H), 7.60 (m, 2H), 7.39-7.23 (m, 9H), 6.67 (br, 1H), 6.50 (br, 1H), 6.40 (br, 1H), 4.57 (m, 1H), 4.32 (m, 3H), 4.17 (m, 3H), 3.98 (m, 1H), 3.81 (m, 1H), 3.68 (m, 2H), 3.30-2.89 (m 4H), 2.80 (m, 2H), 2.65 (m, 1H), 2.42-2.37 (m, 6H), 1.95 (s, 3H), 1.75-1.10 (m, 34H); LRMS for $C_{63}H_{84}N_{10}O_{15}S$, calc'd: 1252.6. found: 1253.9 $[M+H]^+$.

Synthesis of (5S,8S,14S)-2-amino-5-(3-(tert-butoxycarbonylamino)propyl)-18,18-dimethyl-3,6,9,12,16-pentaoxo-8-(3-(3-(2,2,4,6,7-pentamethyl-2,3-dihydrobenzofuran-5-ylsulfonyl)guanidino)propyl)-1-phenyl-17-oxa-2,4,7,10,13-pentaazanonadecane-14-carboxylic acid (Compound 5)

To a round bottom flask containing compound 4 (880 mg, 0.0702 mmol) in DMF (25 ml), were added PS-tris(2-aminoethyl)amine (4.0 g). The reaction was stirred at room temperature for 48 h. The reaction was filtered, concentrated and purified through a short silica gel plug (acetone:CHCl$_3$:MeOH=8:11:1) to afford compound 5 (720 mg, 0.700 mmol, 99.8% yield). $^1$H NMR (400 MHz, d$_6$-DMSO) δ: 8.18-8.12 (m, 4H), 7.36-7.21 (m, 5H), 7.08 (br, 1H), 6.74-6.64 (m, 2H), 6.45-6.40 (br, 2H), 4.60-4.56 (m, 3H), 4.23-4.15 (m, 2H), 3.73 (m 2H), 3.03-2.86 (m, 6H), 2.66-2.62 (m, 2H), 2.56 (m, 1H), 2.47 (s, 3H), 2.45 (m, 1H), 2.42 (s, 3H), 2.00 (s, 3H), 1.65 (m, 2H), 1.52 (m, 2H), 1.41-1.32 (m, 30H); LRMS for $C_{48}H_{74}N_{10}O_{13}S$, calc'd: 1030.5. found: 1031.5 $[M+H]^+$.

Synthesis of tert-butyl 2-((5S,8S,14S)-2-benzyl-5-(4-(tert-butoxycarbonylamino)butyl)-3,6,9,12,15-pentaoxo-8-(3-(3-(2,2,4,6,7-pentamethyl-2,3-dihydrobenzofuran-5-ylsulfonyl)guanidino)propyl)-1,2,4,7,10,13-hexaazacyclopentadecan-14-yl)acetate (Compound 6)

To a round bottom flask containing compound 5 (310 mg, 0.30 mmol) in DCM (150 mL and DMF (30 ml) at ice bath temperature, was added HATU (137 mg, 0.36 mmol), HOBt (49 mg, 0.36 mmol) and 2,4,6-collidine (44 mg, 0.36 mmol). The reaction was stirred at room temperature overnight until LCMS indicates the completion of the reaction. The mixture was concentrated in vacuo and then purified on a silica gel column (acetone:CHCl$_3$, MeOH=2:7:1) to afford compound 6 (300 mg, 99% yield). $^1$H NMR (400 MHz, d$_6$-DMSO) δ: 9.61 (br, 1H), 8.15 (br, 1H), 7.96 (br, 1H), 7.67 (br, 1H), 7.33-7.25 (m, 6H), 6.74-6.65 (m, 2H), 6.40-6.26 (m, 2H), 4.79-4.68 (m, 2H), 4.29-4.00 (m, 5H), 3.05-2.86 (m, 6H), 2.75 (m, 2H), 2.47 (s, 3H), 2.42 (s, 3H), 2.00 (s, 3H), 1.60 (m, 2H), 1.47-1.22 (m, 32H); LRMS for $C_{48}H_{72}N_{10}O_{12}$, calc'd: 1012.5. found: 1013.4 $[M+H]^+$.

Synthesis of 2-((5S,8S,14S)-5-(4-aminobutyl)-2-benzyl-8-(3-guanidinopropyl)-3,6,9,12,15-pentaoxo-1,2,4,7,10,13-hexaazacyclopentadecan-14-yl)acetic acid (Compound 7)

To a round bottom flask containing compound 6 (320 mg, 0.32 mmol), was added a mixed solution of TFA:TIS:water=95:2.5:2.5 (3 ml). The resulting mixture was stirred at room temperature for 20 min. The reaction was concentrated, dissolved in water (20 mL), filtered through a microfilter (0.45 um), and purified by HPLC to afford compound 7 (90 mg, 0.15 mmol, 40% yield). $^1$H NMR (400 MHz, D$_2$O) δ: 7.25-7.15 (m, 5H), 4.58 (s, 2H), 4.35 (m, 1H), 4.25-4.05 (m, 3H), 3.95 (d, J=16.4 Hz, 1H), 3.56 (d, J=16.0 Hz, 1H), 3.10-3.01 (m, 2H), 2.85-2.76 (m, 3H), 2.55 (dd, J=16.0 Hz, 6.4 Hz, 1H), 1.80-1.35 (m, 8H), 1.35-1.20 (m, 2H); $^{13}$C NMR (100 MHz, D$_2$O) δ: 174.6, 174.1, 173.9, 172.2, 171.3, 159.1, 157.0, 129.3, 128.9, 128.3, 55.4, 54.3, 52.1, 50.0, 42.2, 40.7, 39.5, 34.3, 30.2, 26.5, 25.6, 24.7, 22.3; LRMS for $C_{28}H_{40}F_3N_{10}O_8$, calc'd: 701.3. found: 605.4 $[M+H-TFA]^+$.

Consistent with the synthetic schemes presented herein, a series of cycloazapeptide derivatives was synthesized.

An exemplary preparation of one of the cycloazapeptide derivatives of the present application, Compound 9, is shown in Scheme II.

Scheme II

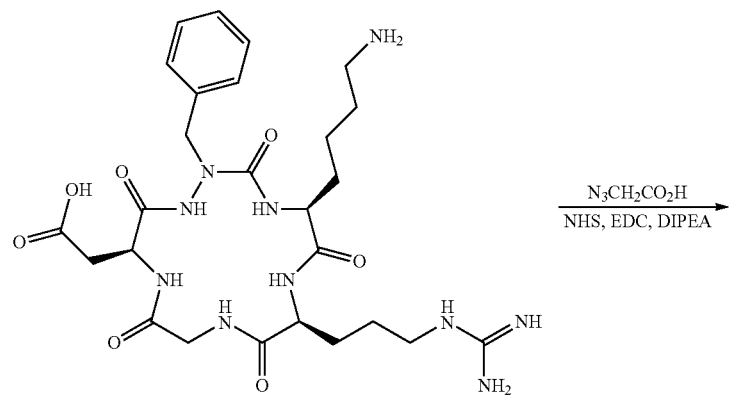

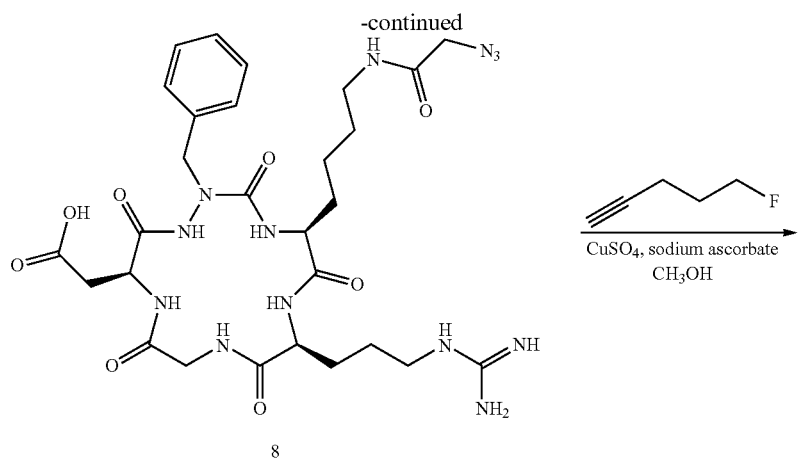

8

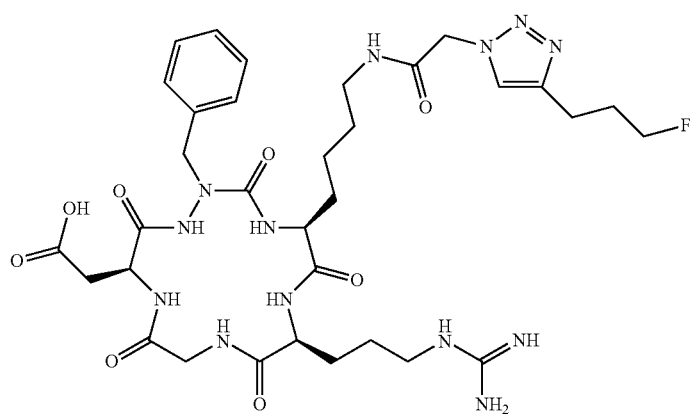

9

Synthesis of Compound 9

Synthesis of 2-((5S,8S,14S)-5-(4-(2-azidoacetamido)butyl)-2-benzyl-8-(3-guanidinopropyl)-3,6,9,12,15-pentaoxo-1,2,4,7,10,13-hexaazacyclopentadecan-14-yl)acetic acid (Compound 8)

To a vial containing azidoglycine (115 mg, 5% wt in DCM/THF, 0.057 mmol) in DMF (0.5 mL) was added N-hydroxysuccinimide (6.6 mg, 0.057 mmol) and EDC (11 mg, 0.057 mmol). After stirring at room temperature for 2 h, compound 7 (33 mg, 0.046 mmol) and DIPEA (13 mg, 0.103 mmol) in DMF (0.5 mL) was added. After another 2 h, the reaction was concentrated, dissolved in water, and purified on HPLC to afford compound 8 (6 mg, 0.014 mmol, 19% yield). $^1$H NMR (400 MHz, D$_2$O) δ: 7.30-7.20 (m, 5H), 4.55-4.50 (m, 1H), 4.40 (m, 1H), 4.30-4.23 (m, 2H), 4.10 (m, 1H), 4.03 (d, J=16.0 Hz, 1H), 3.87 (s, 2H), 3.57 (d, J=16.0 Hz, 1H), 3.11-3.07 (m, 4H), 2.75 (m, 1H), 2.60 (m, 1H), 1.80-1.20 (m, 10H). LRMS for C$_{30}$H$_{41}$F$_3$N$_{13}$O$_9$, calc'd: 784.3. found: 688.3 [M+H−TFA]$^+$.

Synthesis of 2-((5S,8S,14S)-2-benzyl-5-(4-(2-(4-(3-fluoropropyl)-1H-1,2,3-triazol-1-yl)acetamido)butyl)-8-(3-guanidinopropyl)-3,6,9,12,15-pentaoxo-1,2,4,7,10,13-hexaazacyclopentadecan-14-yl)acetic acid (Compound 9)

To a vial containing compound 8 (4.6 mg) in MeOH (0.5 mL), was added CuSO$_4$.5H$_2$O (aqueous, 0.05 M, 2 drops) and sodium ascorbate (aqueous, 0.2 M, 2 drops), 5-fluoropentyne (2 drops). The reaction was stirred at room temperature for 1.5 h and concentrated. The residue was dissolved in water and purified on HPLC to afford compound 9 (2.0 mg, 2.6 umol, 45% yield). $^1$H NMR (400 MHz, D$_2$O) δ: 7.68 (s, 1H), 7.25-7.20 (m, 5H), 5.03 (s, 2H), 4.49-4.45 (m, 3H), 4.35-4.25 (m, 3H), 4.10 (m, 1H), 4.02 (d, J=16.0 Hz, 1H), 3.57 (d, J=16.0 Hz, 1H), 3.13-3.03 (m, 4H), 2.73-2.67 (m, 3H), 2.60 (m, 1H), 1.96-1.85 (m, 2H), 1.75-1.63 (m, 4H), 1.50-1.40 (m, 4H), 1.30-1.20 (m, 2H). LRMS for C$_{35}$H$_{48}$F$_4$N$_{13}$O$_9$, calc'd: 870.4. found: 774.5 [M+H−TFA]$^+$.

Another exemplary preparation of one of the cycloazapeptide derivatives of the present application, Compound 11, is shown in Scheme III.

Scheme III

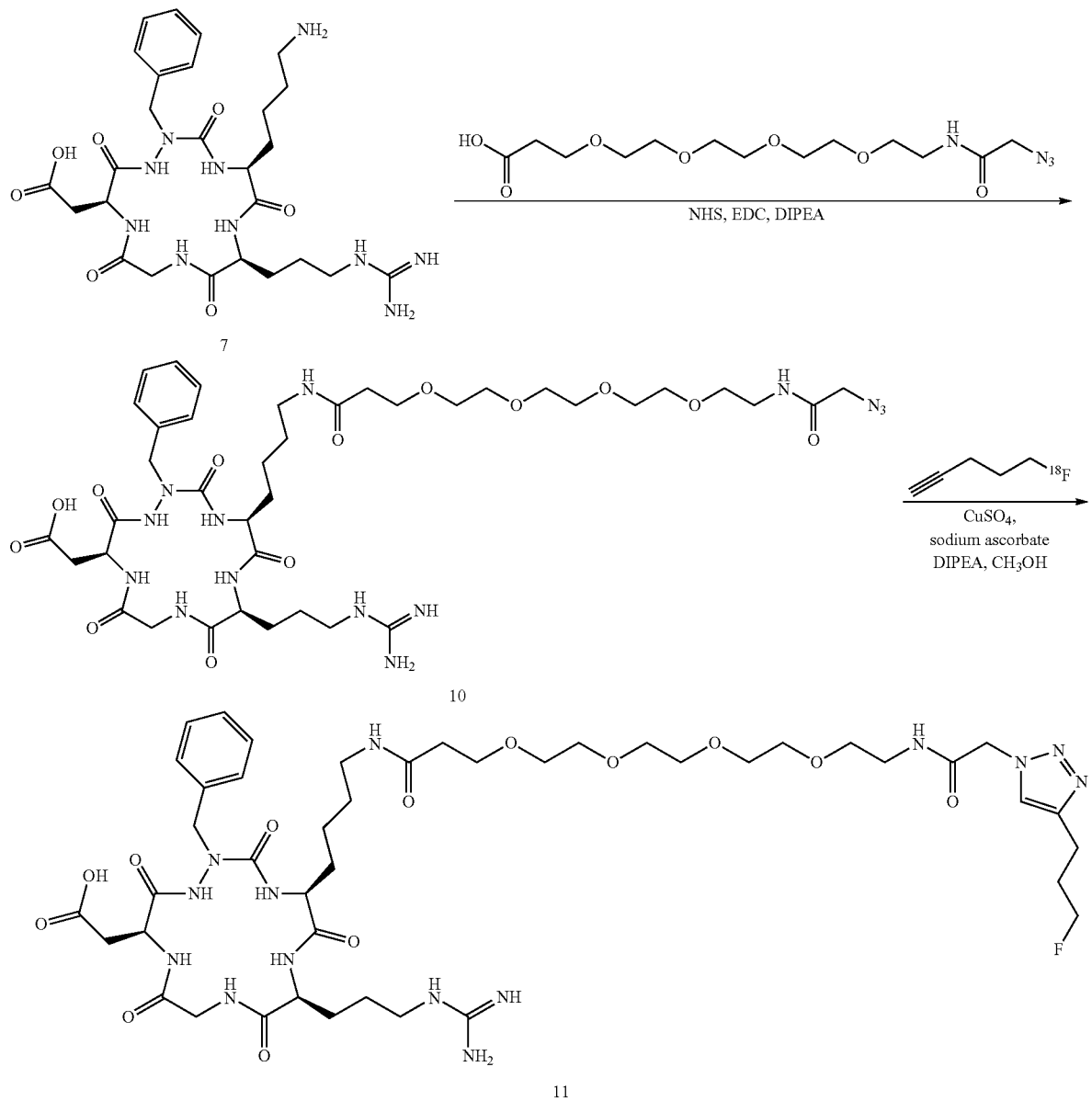

Synthesis of 2-((5S,8S,14S)-5-(1-azido-2,18-dioxo-6,9,12,15-tetraoxa-3,19-diazatricosan-23-yl)-2-benzyl-8-(3-guanidinopropyl)-3,6,9,12,15-pentaoxo-1,2,4,7,10,13-hexaazacyclopentadecan-14-yl)acetic acid (Compound 10)

To a vial containing 1-azido-2-oxo-6,9,12,15-tetraoxa-3-azaoctadecan-18-oic acid (20 mg, 0.057 mmol) in DMF (0.5 mL) was added N-hydroxysuccinimide (6.6 mg, 0.057 mmol) and EDC (11 mg, 0.057 mmol). After stirring at room temperature for 2 h, compound 7 (27 mg, 0.045 mmol) and DIPEA (13 mg, 0.103 mmol) in DMF (0.5 mL) was added. After another 2 h, the reaction was concentrated, dissolved in water, and purified on HPLC to afford compound 10 (4.0 mg, 0.0043 mmol, 7.5% yield). $^1$H NMR (400 MHz, D$_2$O) δ: 7.30-7.20 (m, 5H), 4.55-4.50 (m, 1H), 4.40 (m, 1H), 4.30-4.23 (m, 2H), 4.10 (m, 1H), 4.01 (d, J=16.0 Hz, 1H), 3.87 (s, 2H), 3.77-3.60 (m, 2H), 3.57-3.47 (m, 13H), 3.30 (m, 2H), 3.10-3.04 (m, 4H), 2.75 (m, 1H), 2.59 (m, 1H), 2.48 (m, 2H), 1.80-1.20 (m, 12H). LRMS for $C_{41}H_{62}F_3N_{14}O_{14}$, calc'd: 1031.5. found: 935.6 [M+H−TFA]$^+$.

Synthesis of 2-((5S,8S,14S)-2-benzyl-5-(1-(4-(3-fluoropropyl)-1H-1,2,3-triazol-1-yl)-2,18-dioxo-6,9,12,15-tetraoxa-3,19-diazatricosan-23-yl)-8-(3-guanidinopropyl)-3,6,9,12,15-pentaoxo-1,2,4,7,10,13-hexaazacyclopentadecan-14-yl)acetic acid (Compound 11)

To a vial containing compound 10 (1.3 mg, 1.4 umo) in MeOH (0.5 mL), was added CuSO$_4$.5H$_2$O (aqueous, 0.1 M, 2 drops) and sodium ascorbate (aqueous, 0.5 M, 2 drops), 5-fluoropentyne (2 drops). The reaction was stirred at room temperature for 3 h and concentrated. The residue was dissolved in water and purified on HPLC to afford compound 11 (0.5 mg, 0.5 umol, 38% yield). $^1$H NMR (400 MHz, D$_2$O) δ: 7.68 (s, 1H), 7.25-7.15 (m, 5H), 5.06 (s, 2H), 4.53-4.42 (m, 2H), 4.35-4.22 (m, 3H), 4.10-4.00 (m, 2H), 3.65-3.48 (m, 16H), 3.32 (m, 2H), 3.10-3.00 (m, 4H), 2.75-2.67 (m, 3H), 2.60 (m, 1H), 2.46 (m, 2H), 1.97-1.86 (m, 2H), 1.80-1.60 (m, 4H), 1.50-1.35 (m, 4H), 1.30-1.17 (m, 2H). LRMS for C$_{46}$H$_{69}$F$_4$N$_{14}$O$_{14}$, calc'd: 1117.5. found: 1021.7 [M+H–TFA]$^+$.

Radiosynthesis

Cu(I) catalyzed 'click chemistry' is used to prepare $^{18}$F-radiolabeled RGD cyclic azapeptides. The [$^{18}$F]-fluoroalkyne is prepared using corresponding tosylated alkyne as precursor. Conjugation of [$^{18}$F]fluoroalkyne to cycloazapeptides derivatized with azido group via Cu(I) mediated 1,3-dipolar cycloaddition yields the desired $^{18}$F-labeled products with good yields and excellent radiochemical purity.

An exemplary preparation of one of the $^{18}$F-radiolabeled cyclic azapeptide using click chemistry approach, [$^{18}$F]-compound 11, is shown in Scheme IV.

Synthesis of [$^{14}$]-Compound 11

1-Pentynyl tosylate (15~18 mg) is $^{18}$F-labeled in CH$_3$CN at 110° C. in the presence of K222 and K$_2$CO$_3$ for 5 min while simultaneously distilling the material into a cooled solution containing 1~2 mg of compound 10 in 0.25 mL of acetonitrile, 0.25 ml of ethanol:water 2:1, tris-(benzyltriazolylmethyl)amine (TBTA) (10-20 mg), sodium ascorbate (30-50 mg),\ and 250 μL of 0.1 M CuSO$_4$. The reaction is stirred for 45~60 min at room temperature. The reaction mixture is then loaded onto an HPLC C18 column for purification. After collecting the product, the material is reconstituted via C18 loading and unloading with EtOH and diluting with water to make a 10% EtOH:Water solution. The yields vary from ~35 mCi to ~1 mCi.

Scheme IV

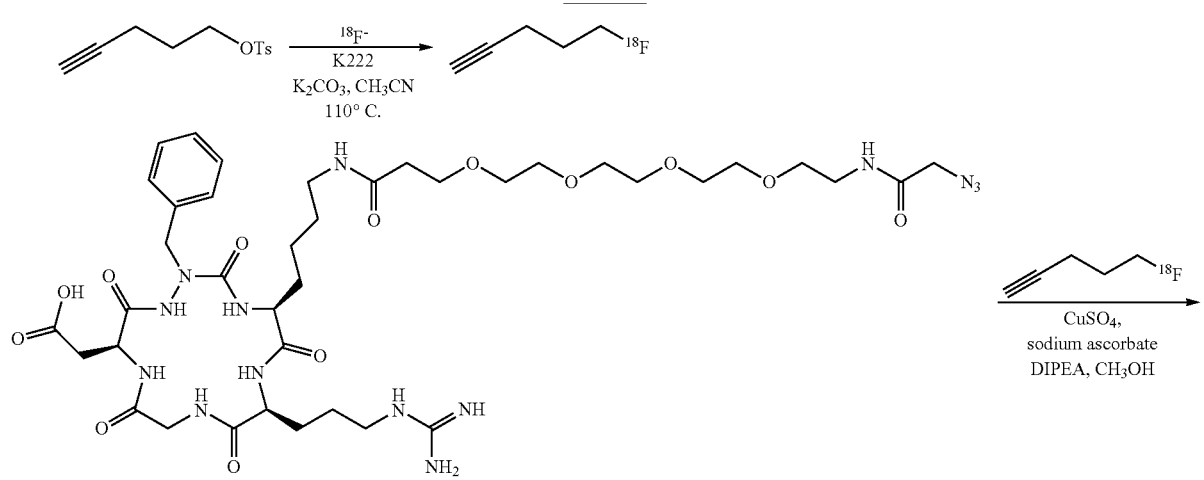

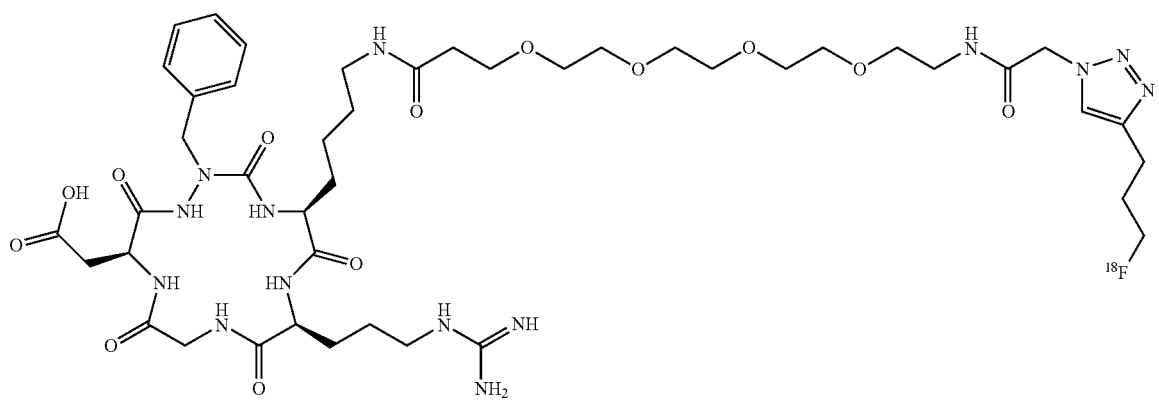

In Vitro Binding Assay:

TABLE 1

RGDfK derivatives employed in in vitro assay

| Compound | Chemical Structure | MW |
|---|---|---|
| 12 | 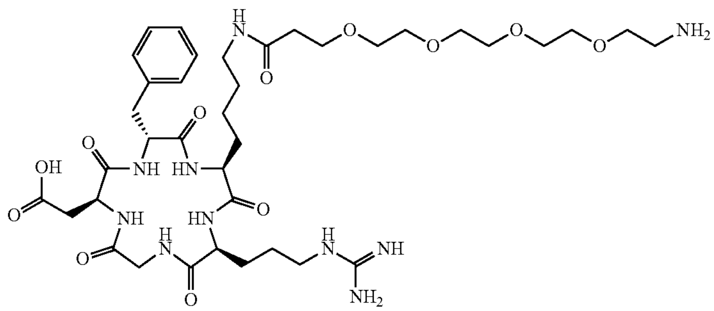 [SMILES: N=C(N)NCCC[C@@H]1NC(=O)[C@H](CCCCNC(=O)CCOCCOCCOCCOCCN)NC(=O)[C@@H](Cc2ccccc2)NC(=O)[C@H](CC(=O)O)NC(=O)CNC1=O] | 850.45 |
| 13 | 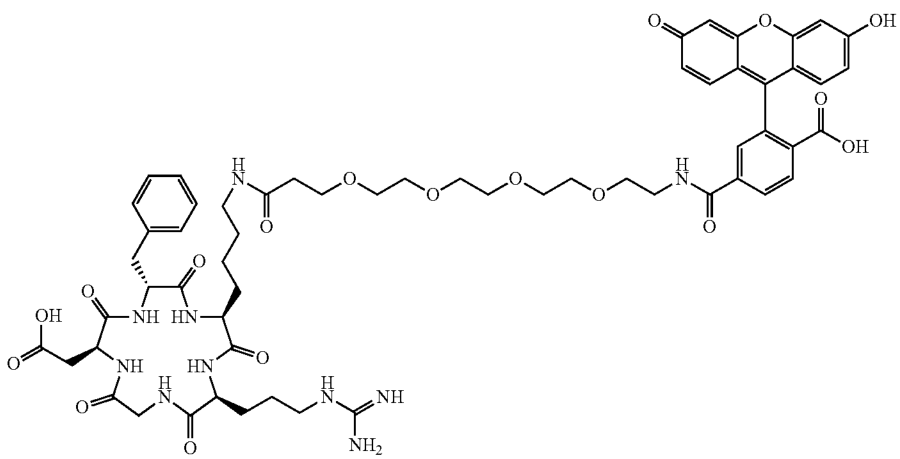 [SMILES: N=C(N)NCCC[C@@H]1NC(=O)[C@H](CCCCNC(=O)CCOCCOCCOCCOCCNC(=O)c2ccc(C(=O)O)c(-c3c4ccc(=O)cc-4oc4cc(O)ccc34)c2)NC(=O)[C@@H](Cc2ccccc2)NC(=O)[C@H](CC(=O)O)NC(=O)CNC1=O] | 1208.50 |

Surface Plasmon Resonance (SPR) Assay:

Compound 12 was immobilized onto a CM5 chip (Supplier: Biacore. CM5 is a SPR chip with a carboxymethylated dextran covalently attached to a gold surface) via amine coupling. Integrin $\alpha_v\beta_3$ samples at 25 nM concentration, premixed with a wide range of concentrations of RGD test compound (0~1000 nM), were flowed through the CM5 chip at 14° C. The interactions between the flowing integrin $\alpha_v\beta_3$ sample and the surface of the chip were recorded by Biacore sensorgram signals. Flow cell #1 served as blank control and the flow cell #2 were coated with compound 1. After subtraction the blank signal of flow cell #1 from the signal of flow cell #2, the resulting sensorgram signals from each cycle were converted into percentage values. Then the $K_d$ and $IC_{50}$ values for each cyclopeptide were calculated.

The results of this 'inverse' integrin $\alpha_v\beta_3$ SPR assay show that cycloazapeptide containing RGD fragment displays surprisingly high binding affinity to integrin $\alpha_v\beta_3$. The $K_d$ and $IC_{50}$ values of cycloazapeptide containing RGD fragment are very close to those of RGDfK, a well-known inhibitor to integrin $\alpha_v\beta_3$. See FIG. 1.

Cell-Based Integrin Binding Competition Assay:

Integrin $\alpha_v\beta_3$ expressing U87MG cells were incubated with a series of concentration of RGD compounds (0-32 μM) in the presence of 2 μM of green fluorescence labeled compound 13 for 2 hrs. After incubation, cells were washed three times to eliminate unbound RGD compounds. Fluorescence readings (RLU) were then taken (excitation at 491 nm, emission at 518 nm, cutoff 515 nm).

Figure 2:
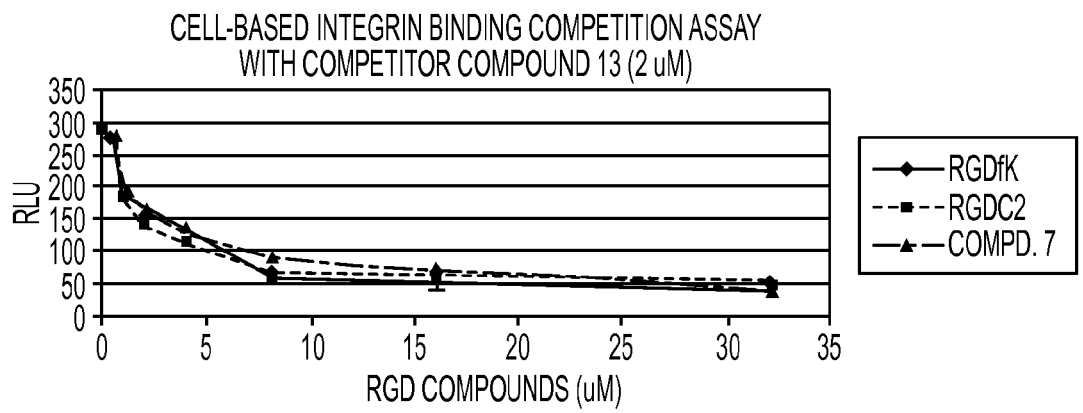
FIG. 2 is a graph of binding affinity determination of cyclo-peptides using cell-based binding assay.
Figure 2:
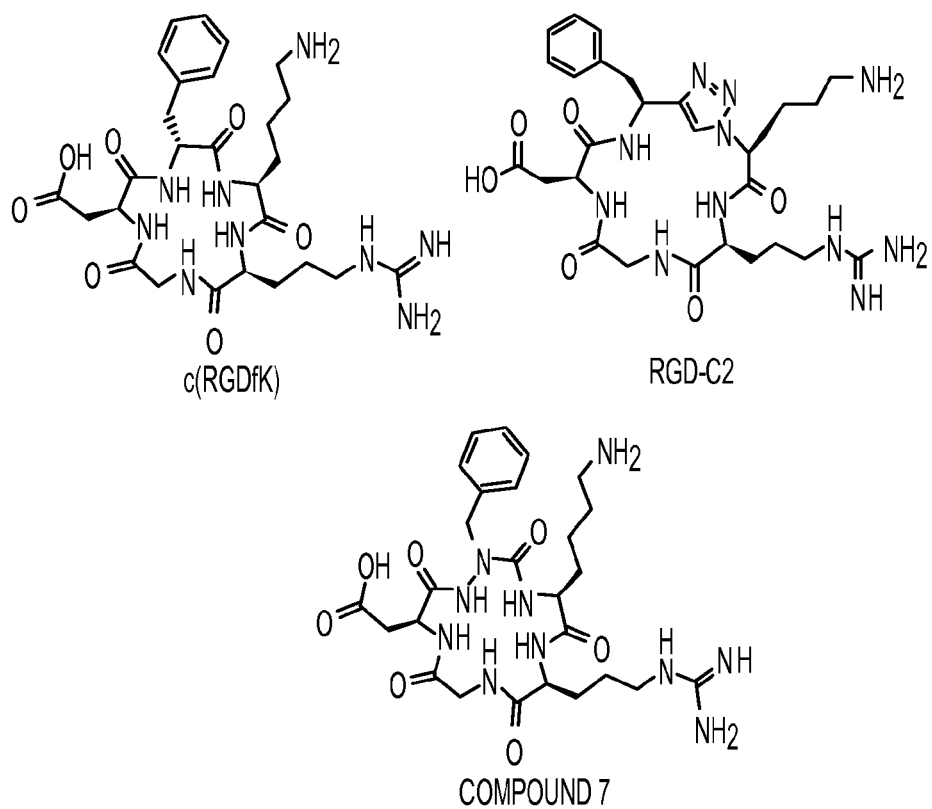

The results are consistent with that of surface plasmon resonance assay. The data further demonstrate that compound 7 and RGDfK are very similar in potency. See FIG. 2.

All references cited herein are incorporated by reference as if each had been individually incorporated by reference in its entirety. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

1. Aumailley, M.; Gurrath, M.; Muller, G.; Calvete, J.; Timpl, R.; Kessler, H. FEBS Lett. 1991, 291, 50-54.
2. Chen, X.; Park, R.; Shahinian, A. H.; Bading, J. R.; Conti, P. S, Nucl. Med. Biol., 2004, 31, 11-19.
3. Chen, X.; Park, R.; Hou, Y.; Khankaldyyan, V.; Gonzales-Gomez, I.; Tohme, M.; et al. Eur. J. Nul. Med. Mol. Imaging, 2004, 31, 1081-1089.

4. Chen, X.; Hou, Y.; Tohme, M.; Park, R.; Khankaldyyan, V.; Gonzales-Gomez, I.; et al. *J. Nul. Med.*, 2004, 45, 1776-1783.

5. Haubner, R.; Weber, W. A.; Beer, A. J.; Vabuliene, E.; Reim, D.; Sarbia, M.; Becker, K. F.; Goebel, M., et al. *PLoS Med.*, 2005, 2, e70.

6. Haubner, R.; Wester, H. J.; Weber, W. A.; Mang, C.; Ziegler, S. I.; Goodman, S. L.; Senekowisch-Schmidtke, R.; Kessler, H.; Schwaiger, M. *Cancer Res.*, 2001, 61, 1781-1785.

7. Haubner, R.; Kuhnast B,; Mang, C.; Weber W. A.; Kessler, H.; Wester, H. J.; Schwaiger, M. *Bioconjug. Chem.*, 2004, 15, 61-69.

8. Belvisi, L.; Bernardi, A.; Checchia, A.; et al. *Org. Lett.*, 2001, 3, 1001-1004.

9. Kolb, H. C.; Finn, M. G.; Sharpless, K. B. *Angew. Chem. Int. Ed.*, 2001, 40, 2004-2021.

10. Kolb, H. C.; Sharpless, K. B. *Drug Discovery Today*, 2003, 8, 1128-1137.

11. Rostovtsev, V. V.; Green, L. G.; Fokin, V. V.; Sharpless, K. B. *Angew. Chem. Int. Ed.*, 2002, 41, 2596-2599.

12. Tornøe, C. W.; Christensen, C.; Meldal, M. *J. Org. Chem.*, 2002, 67, 3057-3064.

13. Wang, Q.; Chan, T. R.; Hilgraf, R.; Fokin, V. V.; Sharpless, K. B.; Finn, M. G. *J. Am. Chem. Soc.*, 2003, 125, 3192-3193.

14. Lee, L. V.; Mitchell, M. L.; Huang, S.-J.; Fokin, V. V.; Sharpless, K. B.; Wong, C.-H. *J. Am. Chem. Soc.*, 2003, 125, 9588-9589.

15. Lewis, W. G.; Green, L. G.; Grynszpan, F.; Radic, Z.; Carlier, P. R.; Taylor, P.; Finn, M. G.; Barry, K. *Angew. Chem., Int. Ed.*, 2002, 41, 1053-1057.

16. Manetsch, R.; Krasinski, A.; Radic, Z.; Raushel, J.; Taylor, P.; Sharpless, K. B.; Kolb, H. C. *J. Am. Chem. Soc.*, 2004, 126, 12809-12818.

17. Mocharla, V. P.; Colasson, B.; Lee, L. V.; Roeper, S.; Sharpless, K. B.; Wong, C.-H.; Kolb, H. C. *Angew. Chem. Int. Ed.*, 2005, 44, 116-120.

What is claimed:

1. A method for imaging of blood vessel growth in solid tumors based on expression of integrin $\alpha_v\beta_3$ within the body of a patient, the method comprising:

(a) administering to the patient a radiolabeled cycloazapeptide;

(b) employing a nuclear imaging technique selected from the group consisting of positron emission tomography (PET) and single photon emission computed tomography (SPECT) for imaging a distribution of the radiolabeled cycloazapeptide within the body or within a portion thereof; and (c) correlating the distribution of the radiolabeled cycloazapeptide to the growth of blood vessels in solid tumors, wherein the radiolabeled cycloazapeptide is of formula II:

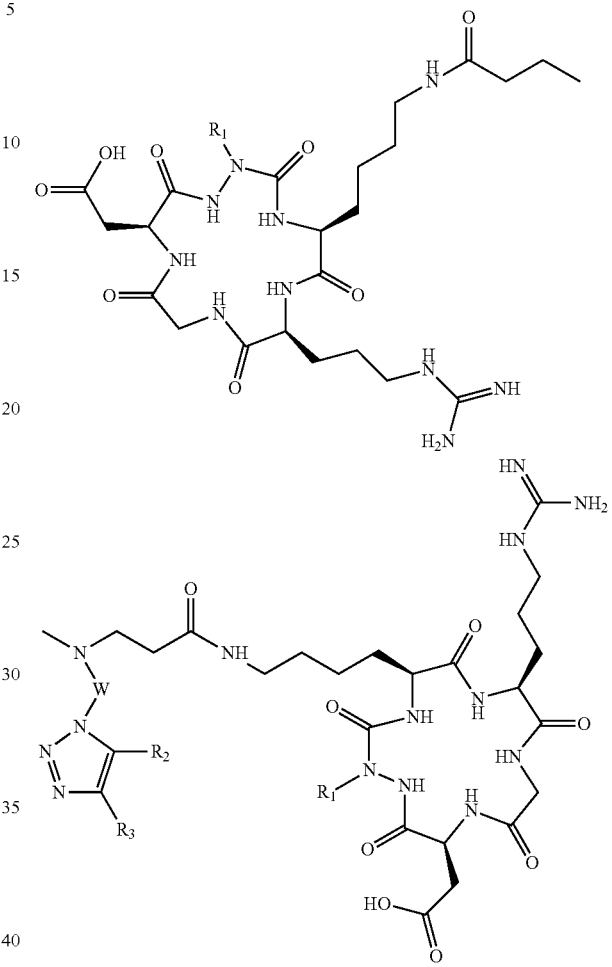

wherein:

each $R_1$ is hydrogen or is independently selected from the group consisting of a side chain of a natural amino acid and a side chain of an unnatural amino acid;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, alkoxyalkyl, aryl, carbocycle and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{75}$Br, $^{124}$I, $^{125}$I and $^{131}$I; and W is

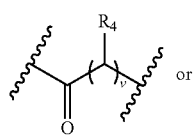

or

-continued

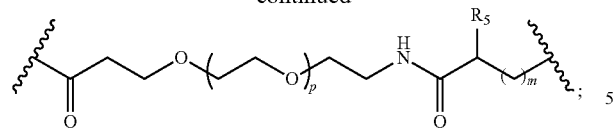

where p is an integer between 0 and 15;
v is 0, 1, 2, or 3;
m is 0, 1 or 2;

each $R_4$ is independently selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted;
$R_5$ is selected from the group consisting of —H, $C_1$-$C_6$ alkyl, $C_2$-$C_6$ alkenyl and $C_2$-$C_6$ alkynyl, wherein the alkyl, alkenyl and alkynyl groups are each optionally substituted and wherein the configuration of the chiral center that is substituted with the $R_5$ substituent is R or S or mixtures thereof;
or a pharmaceutically acceptable salt thereof, optionally in the form of a single stereoisomer or mixture of stereoisomers thereof.

2. The method of claim 1 wherein:
each $R_1$ is benzyl;
$R_2$ is H;
$R_3$ is an optionally substituted $C_1$-$C_6$ alkyl comprising a radionuclide selected from the group consisting of $^{11}C$, $^{13}N$, $^{15}O$, $^{18}F$, $^{75}Br$, $^{124}I$, $^{125}I$ and $^{131}I$;
and W is

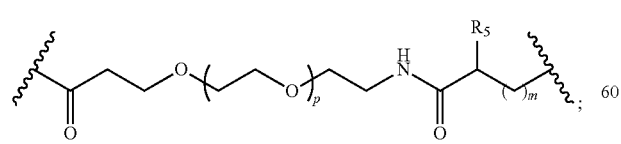

where p is 0, 1, 2, 3, 4 or 5.

3. A method of monitoring the level of integrin $\alpha_v\beta_3$ or visualizing integrin $\alpha_v\beta_3$ expression within a body of a patient, the method comprising:

(a) administering to the patient a radiolabeled cycloazapeptide; and
(b) employing a nuclear imaging technique selected from the group consisting of positron emission tomography (PET) and single photon emission computed tomography (SPECT) for monitoring or visualizing a distribution of the radiolabeled cycloazapeptide within the body or within a portion thereof,
wherein the radiolabeled cycloazapeptide is of formula II:

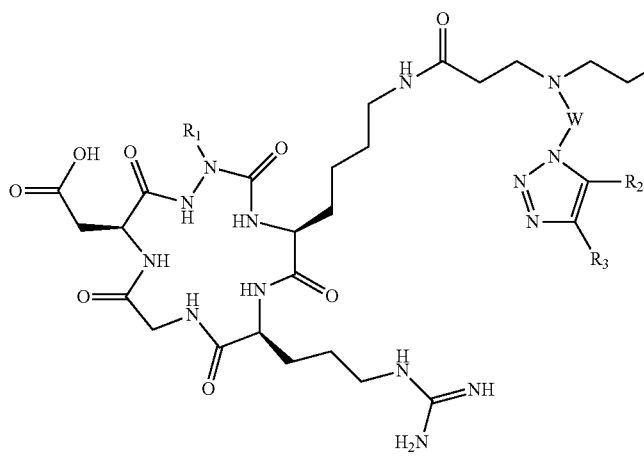

wherein:
each $R_1$ is hydrogen or is independently selected from the group consisting of a side chain of a natural amino acid and a side chain of an unnatural amino acid;
$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, alkoxyalkyl, aryl, carbocycle and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$ and $^{131}I$; and
W is

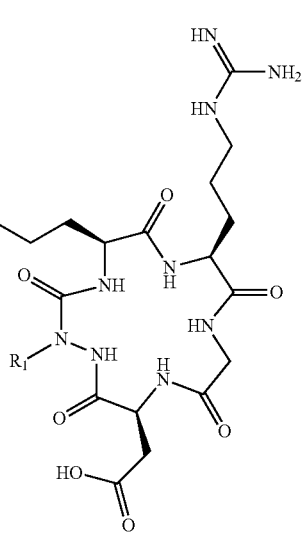

where p is an integer between 0 and 15;

v is 0, 1, 2, or 3;

m is 0, 1 or 2;

each $R_4$ is independently selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted;

$R_5$ is selected from the group consisting of —H, $C_1$-$C_6$ alkyl, $C_2$-$C_6$ alkenyl and $C_2$-$C_6$ alkynyl, wherein the alkyl, alkenyl and alkynyl groups are each optionally substituted and wherein the configuration of the chiral center that is substituted with the $R_5$ substituent is R or S or mixtures thereof;

or a pharmaceutically acceptable salt thereof, optionally in the form of a single stereoisomer or mixture of stereoisomers thereof.

4. The method of claim 3 wherein:

each $R_1$ is benzyl;

$R_2$ is H;

$R_3$ is an optionally substituted $C_1$-$C_6$ alkyl comprising a radionuclide selected from the group consisting of $^{11}C$, $^{13}N$, $^{15}O$, $^{18}F$, $^{75}B$, $^{124}I$, $^{125}I$ and $^{131}I$;

and W is

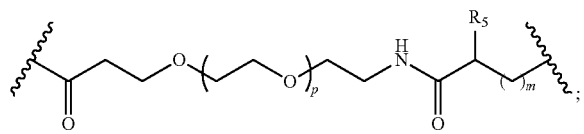

where p is 0, 1, 2, 3, 4 or 5.

5. A method of monitoring the level of integrin $\alpha_v\beta_3$ or visualizing integrin $\alpha_v\beta_3$ expression within a body of a patient, the method comprising:

(a) administering to the patient a radiolabeled cycloazapeptide; and (b) employing a nuclear imaging technique selected from the group consisting of positron emission tomography (PET) and single photon emission computed tomography (SPECT) for monitoring or visualizing a distribution of the radiolabeled cycloazapeptide within the body or within a portion thereof;

wherein the radiolabeled cycloazapeptide is of formula I:

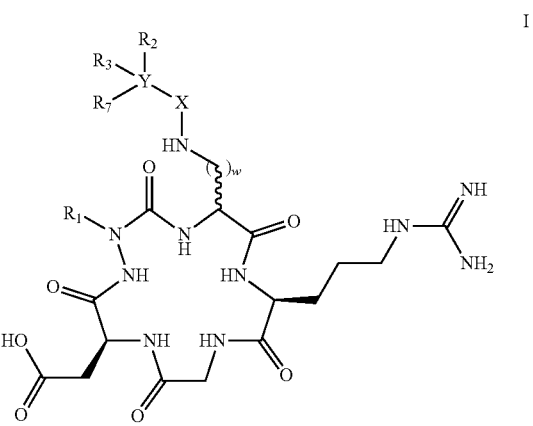

wherein $R_1$ is hydrogen or is selected from the group consisting of a side chain of a natural amino acid and a side chain of an unnatural amino acid;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle and heterocycle, groups are each optionally substituted;

$R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle and a 3- to 7-membered heterocycle, wherein the alkyl, alkenyl, alkynyl, arylalkylene, carbocycle and heterocycle groups are each optionally substituted; wherein $R_2$, $R_3$ and $R_7$ are not all H;

X is a 5 or 6-membered heterocycle or a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic and sugar moiety, or a combination thereof;

Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic and sugar moiety;

where at least one of X and Y is a 5 or 6-membered heterocycle; and w is 1, 2, 3, 4 or 5;

wherein any one of X, Y, $R_2$, $R_3$, and $R_7$ comprises a radionuclide selected from the group consisting of positron or gamma emitters.

6. The method of claim 5, wherein the radiolabeled cycloazapeptide is selected from the group consisting of:

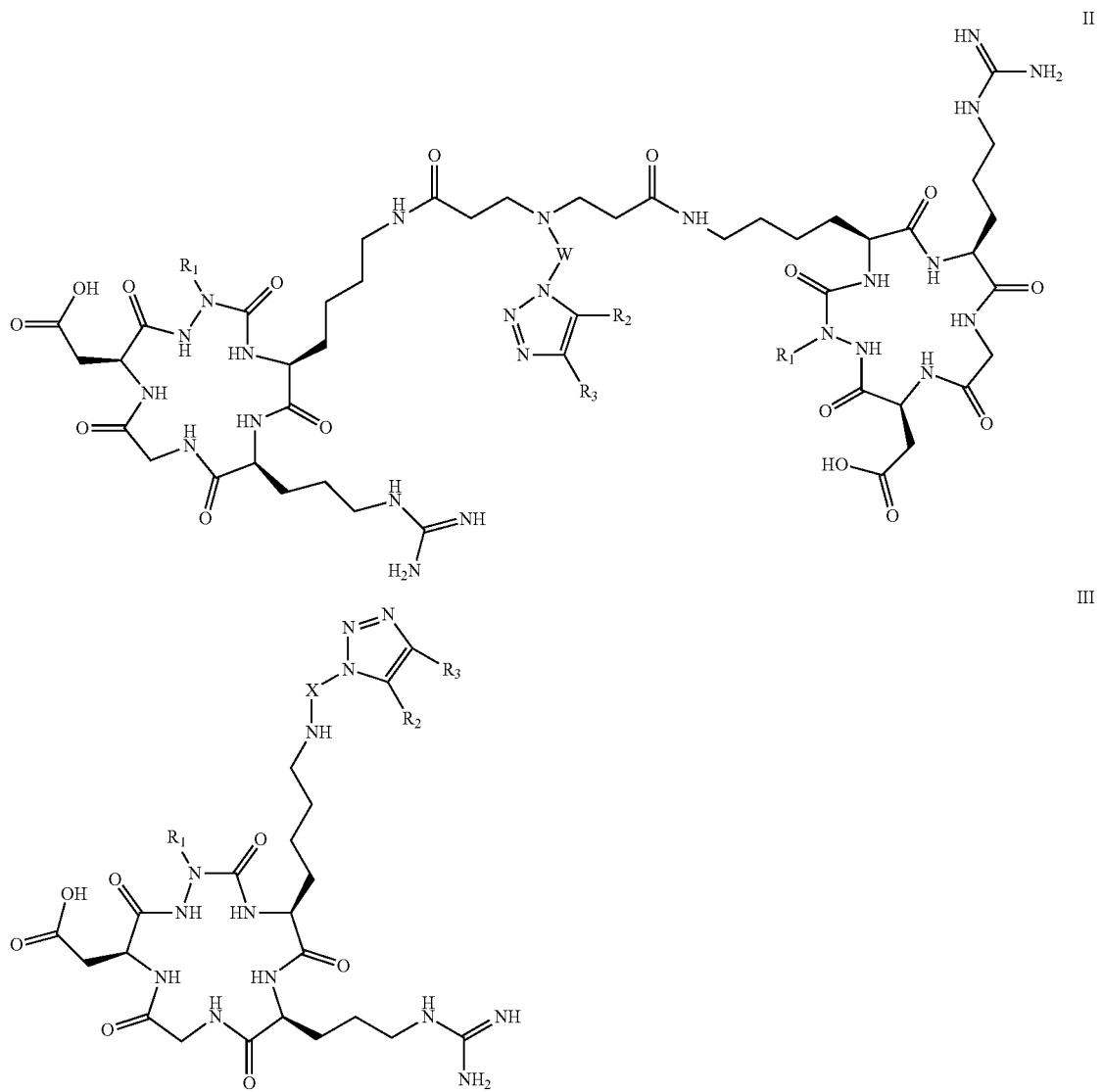

wherein each $R_1$ is hydrogen or is independently selected from the group consisting of a side chain of a natural amino acid and a side chain of an unnatural amino acid;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, alkoxyalkyl, aryl, carbocycle and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P;

each of X and W is selected from the group consisting of:

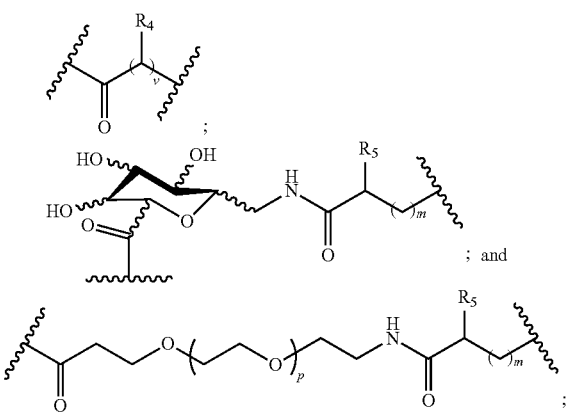

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl and a PEG moiety, wherein the alkyl, alkenyl, alkynyl, alkoxy, aryl, carbocycle and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle and heterocycle, groups are each optionally substituted;

wherein the configuration of the chiral centers is R or S or mixtures thereof;

v is 0, 1, 2, 3 or 4;

m is 0, 1, 2, 3 or 4; and p is an integer between 1 and 25.

7. The method of claim 5, wherein Y is a 5 or 6-membered heterocycle; and X is a linker either comprising a sugar mimetic selected from the group consisting of a 4 to 6-membered carbocycle substituted with at least one hydroxyl group and a 5- to 6-membered heterocycle substituted with at least one hydroxyl group or comprising a sugar moiety selected from the group consisting of glucose and galactose.

8. The method of claim 6 wherein:

Y is a 5 or 6-membered heterocycle;

X is selected from the group consisting of:

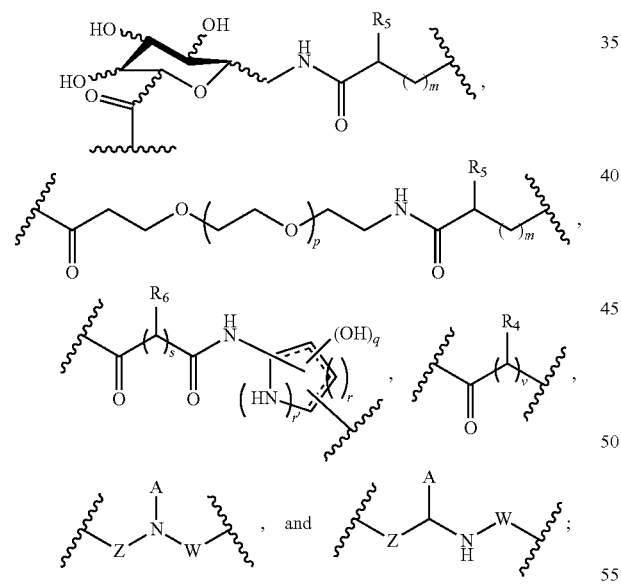

wherein Z is selected from the group consisting of:

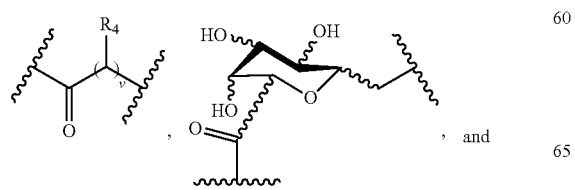

W is selected from the group consisting of:

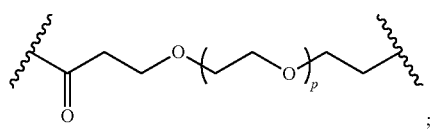

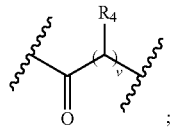

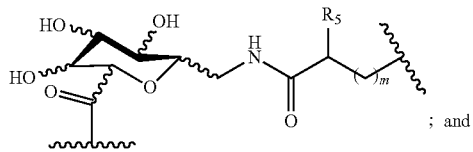

A is selected from the group consisting of:

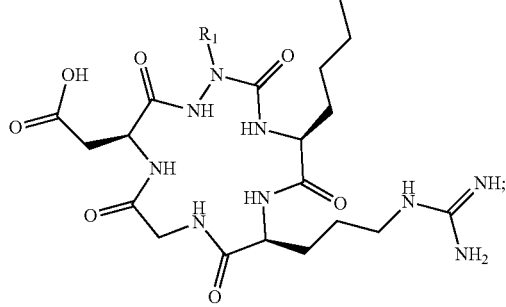

-continued

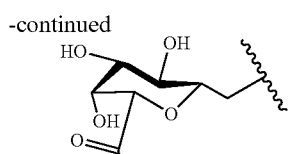

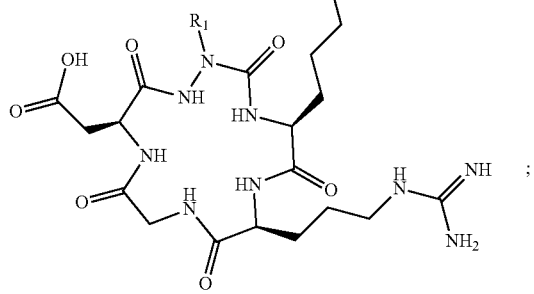
; and

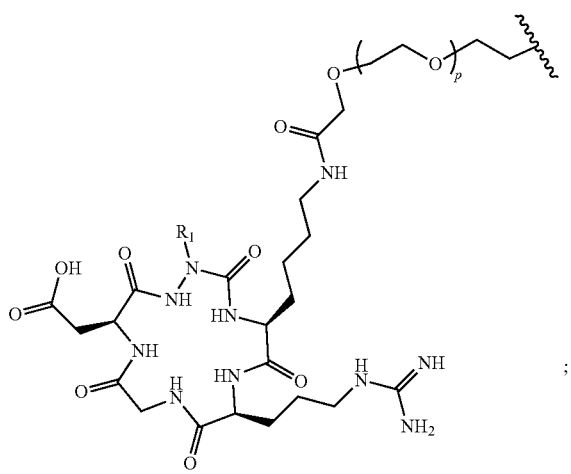
;

each $R_1$ is independently selected from the group consisting of a side chain of a natural amino acid and a side chain of an unnatural amino acid;

each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl and a PEG moiety, wherein the alkyl, alkenyl, alkynyl, alkoxy, aryl, carbocycle and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, aryl, carbocycle and heterocycle groups are each optionally substituted;

each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl and $C_1$-$C_6$-alkoxy-$C_1$-$C_6$-alkyl, wherein the alkyl, alkenyl, alkynyl, alkyloxy and aryl-alkylene groups are each optionally substituted;

each v is 0, 1, 2, 3 or 4;

m is 0, 1, 2, 3 or 4;

p is an integer between 1 and 110;

q is 1, 2, 3 or 4;

r is 1, 2 or 3;

r' is 0 or 1;

s is 1, 2, 3 or 4; and the radionuclide is selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P;

wherein the configuration of the chiral centers is R or S or mixtures thereof.

9. The method of claim 8, wherein:

$R_1$ is a side chain of a natural amino acid;

$R_7$ is absent;

X is

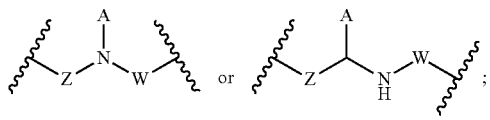

Y is 1,2,3-triazolyl; and $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, alkoxyalkyl, aryl, carbocycle and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{75}$B, $^{124}$I, $^{125}$I and $^{131}$I.

10. A method for imaging of blood vessel growth in solid tumors based on expression of integrin $\alpha_v\beta_3$ within the body of a patient, the method comprising:

(a) administering to the patient a radiolabeled cycloazapeptide;

(b) employing a nuclear imaging technique selected from the group consisting of positron emission tomography (PET) and single photon emission computed tomography (SPECT) for imaging a distribution of the radiolabeled cycloazapeptide within the body or within a portion thereof; and (c) correlating the distribution of the radiolabeled cycloazapeptide to the growth of blood vessels in solid tumors, wherein the radiolabeled cycloazapeptide is selected from the group consisting of:

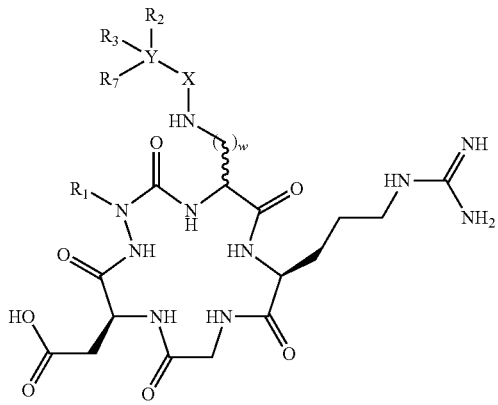

wherein:
R₁ is hydrogen or is selected from the group consisting of a side chain of a natural amino acid and a side chain of an unnatural amino acid;

R₂ and R₃ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, alkoxyalkyl, aryl, carbocycle and heterocycle, groups are each optionally substituted;

R₇ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein R₂, R₃ and R₇ are not all H;

X is a 5 or 6-membered heterocycle or a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic and sugar moiety, or a combination thereof;

Y is a 5 or 6-membered heterocycle or a linker comprising a hydrophilic moiety selected from the group consisting of hydroxyl, carbonyl, sulfonamide, sulfonate, phosphate, polar amino acid moiety, PEG moiety, sugar mimetic and sugar moiety;

where at least one of X and Y is a 5 or 6-membered heterocycle; and w is 1, 2, 3, 4 or 5;

wherein any one of X, Y, R₂, R₃, and R₇ comprises a radionuclide selected from the group consisting of positron or gamma emitters; and

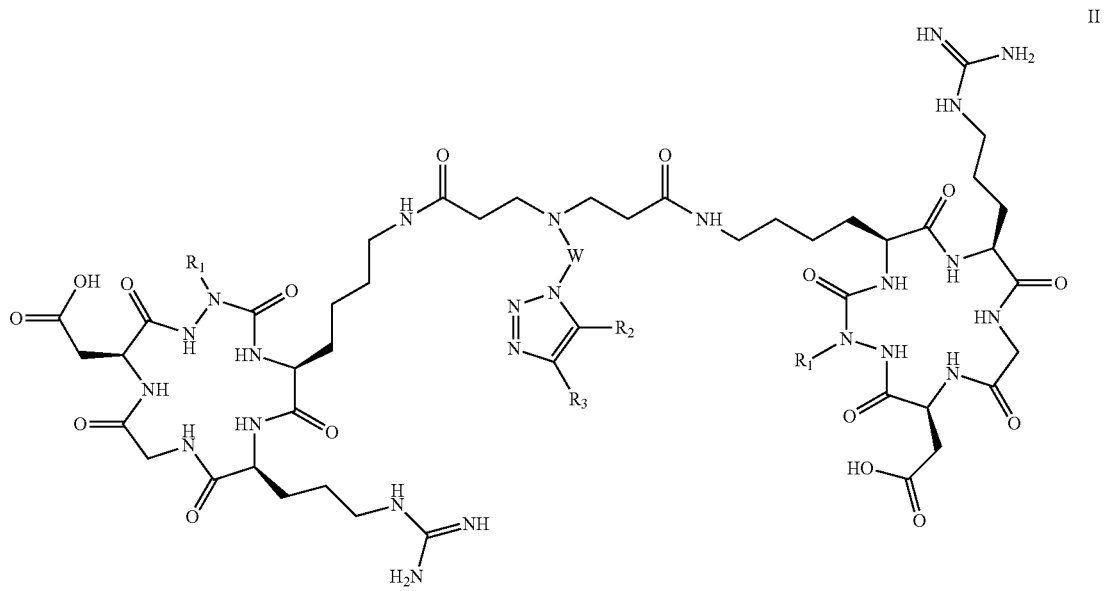

-continued

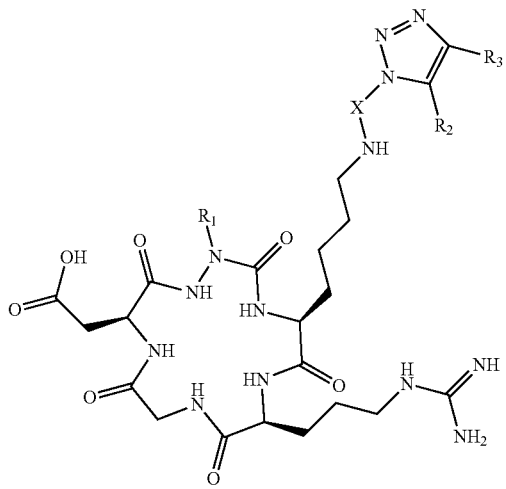

III wherein:

each $R_1$ is hydrogen or is independently selected from the group consisting of a side chain of a natural amino acid and a side chain of an unnatural amino acid;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$;

each of X and W is selected from the group consisting of:

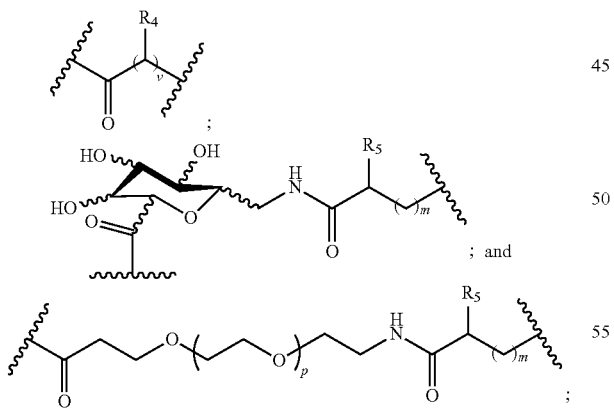

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, aryl, carbocycle and heterocycle groups are each optionally substituted;

wherein the configuration of the chiral centers is R or S or mixtures thereof;

v is 0, 1, 2, 3 or 4;

m is 0, 1, 2, 3 or 4; and p is an integer between 1 and 25.

11. The method of claim 10, wherein Y is a 5 or 6-membered heterocycle; and X is a linker either comprising a sugar mimetic selected from the group consisting of a 4 to 6-membered carbocycle substituted with at least one hydroxyl group and a 5- to 6-membered heterocycle substituted with at least one hydroxyl group or comprising a sugar moiety selected from the group consisting of glucose and galactose.

12. The method of claim 10, wherein:

Y is a 5 or 6-membered heterocycle;

X is selected from the group consisting of:

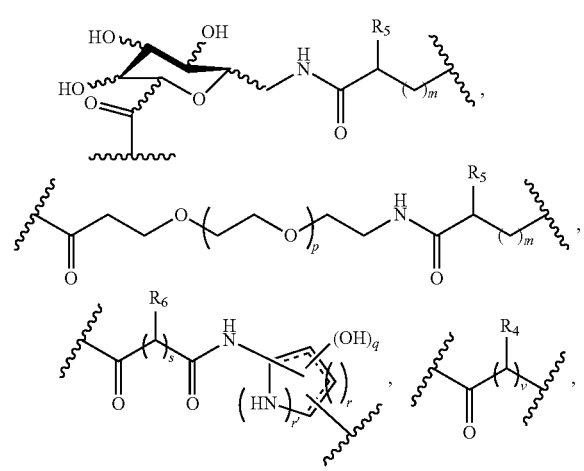

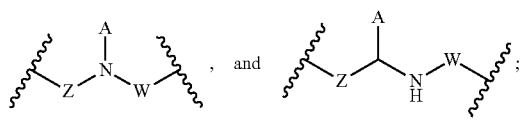, and wherein Z is selected from the group consisting of:

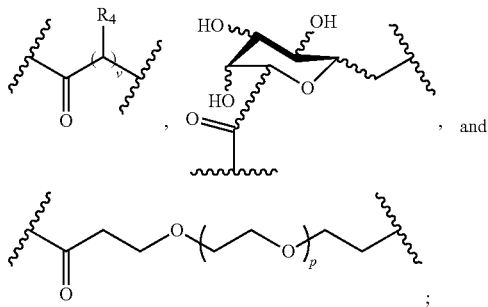

W is selected from the group consisting of:

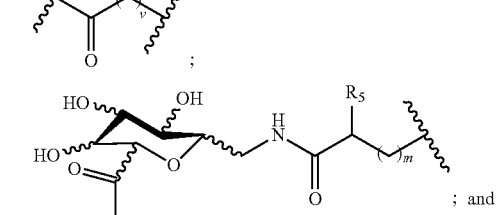

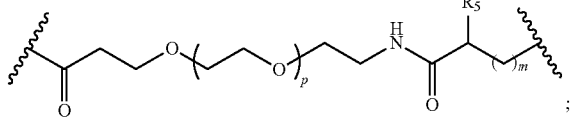

A is selected from the group consisting of:

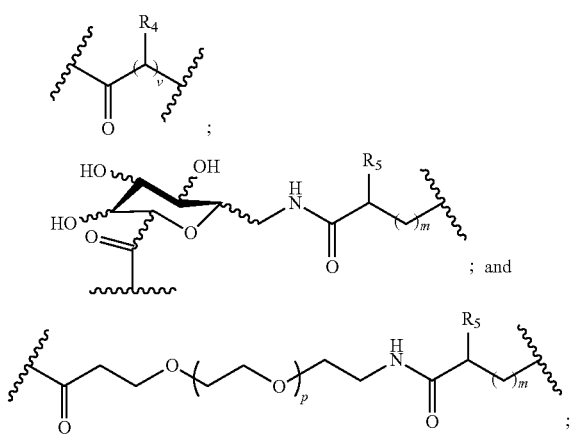

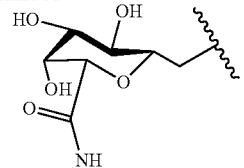

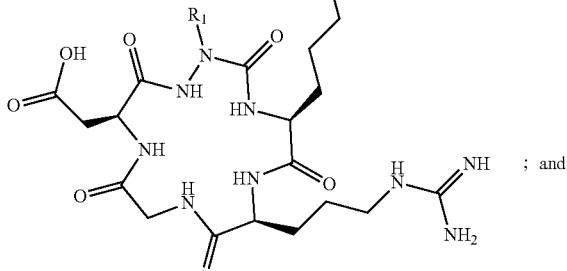; and

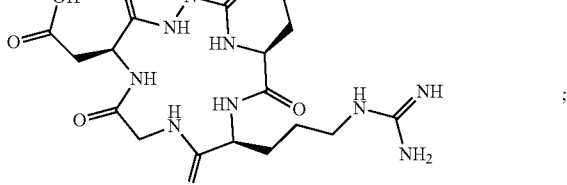;

each $R_1$ is independently selected from the group consisting of a side chain of a natural amino acid and a side chain of an unnatural amino acid;

each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl and a PEG moiety, wherein the alkyl, alkenyl, alkynyl, alkoxy, aryl, carbocycle and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, aryl, carbocycle and heterocycle, groups are each optionally substituted;

each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl and $C_1$-$C_6$-alkoxy-$C_1$-$C_6$-alkyl, wherein the alkyl, alkenyl, alkynyl, alkyloxy and aryl-alkylene groups are each optionally substituted;

each v is 0, 1, 2, 3 or 4;
m is 0, 1, 2, 3 or 4;
p is an integer between 1 and 110;
q is 1, 2, 3 or 4;

r is 1, 2 or 3;
r' is 0 or 1;
s is 1, 2, 3 or 4; and
the radionuclide is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$;
wherein the configuration of the chiral centers is R or S or mixtures thereof.

13. The method of claim 12, wherein:
$R_1$ is a side chain of a natural amino acid;
$R_7$ is absent;
X is

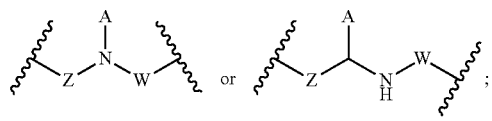

Y is 1,2,3-triazolyl; and
$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, alkoxyalkyl, aryl, carbocycle and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$ and $^{131}I$.

14. A method for imaging of blood vessel growth in solid tumors based on expression of integrin $\alpha_v\beta_3$ within the body of a patient, the method comprising:
(a) administering to the patient a radiolabeled cycloazapeptide;
(b) employing a nuclear imaging technique selected from the group consisting of positron emission tomography (PET) and single photon emission computed tomography (SPECT) for imaging a distribution of the radiolabeled cycloazapeptide within the body or within a portion thereof; and
(c) correlating the distribution of the radiolabeled cycloazapeptide to the growth of blood vessels in solid tumors,
wherein the radiolabeled cycloazapeptide is selected from the group consisting of:

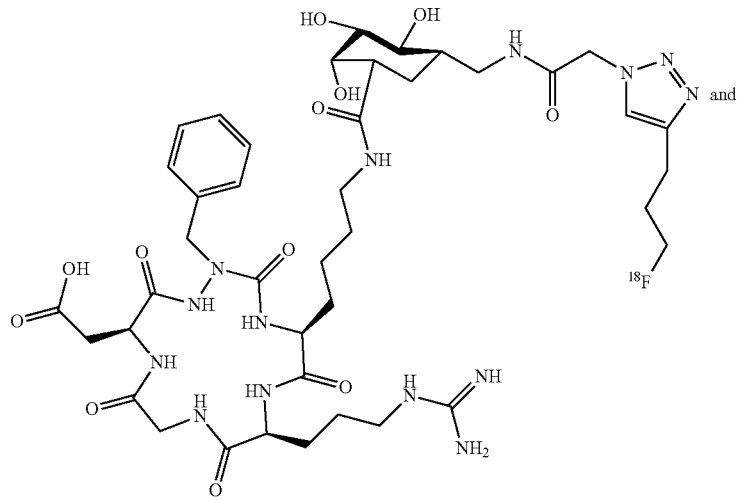

and

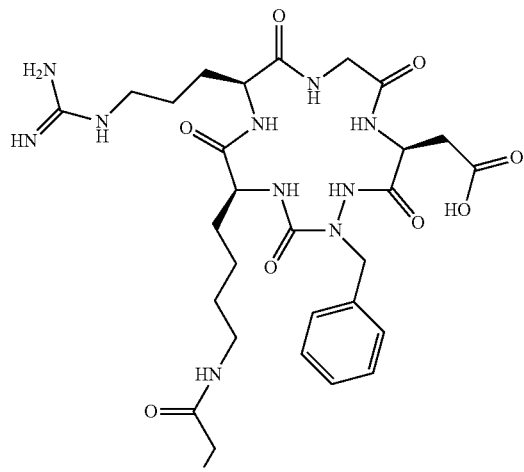

-continued

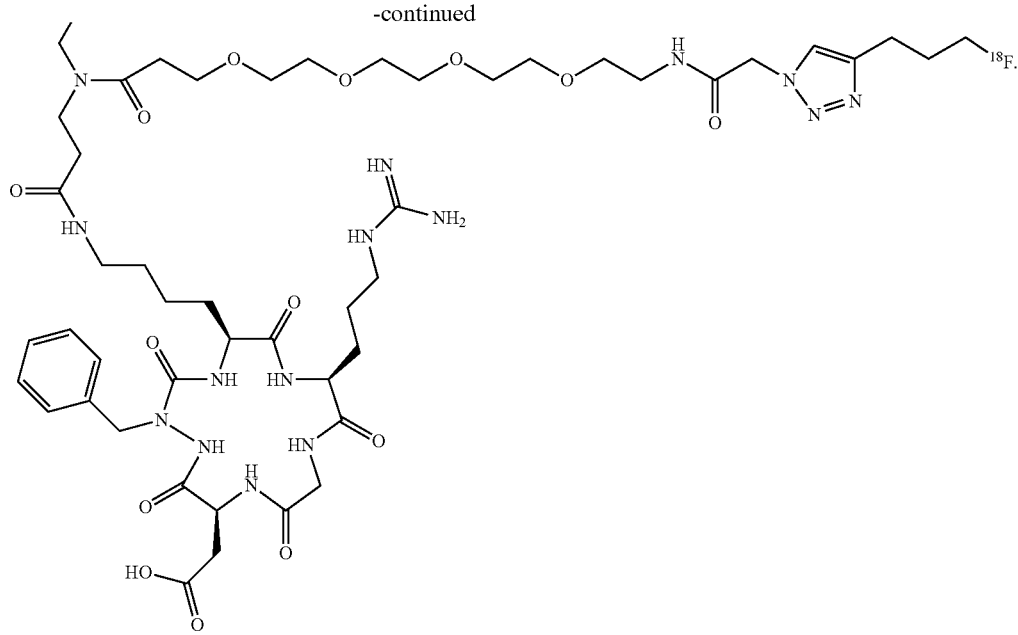

15. A method for selectively binding integrin receptors in a mammal, the method comprising administering a therapeutically effective amount of a cycloazapeptide of the formula Z:

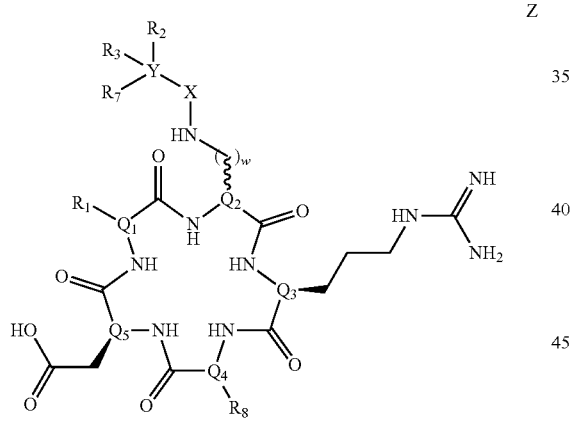

wherein:
each $Q_1$, $Q_2$, $Q_3$, $Q_4$ and $Q_5$ is independently —CH— or N, provided that at least one of $Q_1$, $Q_2$, $Q_3$, $Q_4$ and $Q_5$ is N;
$R_1$ is hydrogen or is selected from the group consisting of a side chain of a natural amino acid and a side chain of an unnatural amino acid;
$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl and $C_1$-$C_6$-alkoxy-$C_1$-$C_6$-alkyl, wherein the alkyl, alkenyl, alkynyl, alkyloxy, alkoxyalkyl, aryl, carbocycle and heterocycle groups are each optionally substituted;
$R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein $R_2$, $R_3$ and $R_7$ are not all H;
$R_8$ is hydrogen or is selected from the group consisting of a side chain of a natural amino acid and a side chain of an unnatural amino acid;
X is a 5 or 6-membered heterocycle or a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic and sugar moiety, or a combination thereof;
Y is a 5 or 6-membered heterocycle or a linker comprising a hydrophilic moiety selected from the group consisting of hydroxyl, carbonyl, sulfonamide, sulfonate, phosphate, polar amino acid moiety, PEG moiety, sugar mimetic and sugar moiety;
where at least one of X and Y is a 5 or 6-membered heterocycle; and
w is 1, 2, 3, 4 or 5;
or a pharmaceutical composition thereof.

16. The method of claim 5, further comprising:
(c) administering to the patient, a therapeutic agent;
(d) administering to the patient the radiolabeled cycloazapeptide; and
(e) employing the nuclear imaging technique for monitoring or visualizing a distribution of the radiolabeled cycloazapeptide within the body or within a portion thereof.

17. A method of monitoring the level of integrin receptor expression within a body of a patient, the method comprising:
(a) administering to the patient a radiolabeled cycloazapeptide; and
(b) employing a nuclear imaging technique selected from the group consisting of positron emission tomography (PET) and single photon emission computed tomography (SPECT) for monitoring or visualizing a distribution of the radiolabeled cycloazapeptide within the body or within a portion thereof;

wherein the radiolabeled cycloazapeptide is:

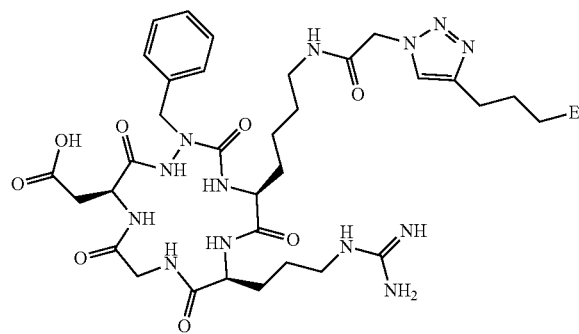

where E is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$, or a pharmaceutically acceptable salt thereof, optionally in the form of a single stereoisomer or mixture of stereoisomers thereof.

18. The method of claim 17 wherein E is $^{18}F$.

19. The method of claim 10, wherein the radiolabeled cycloazapeptide is:

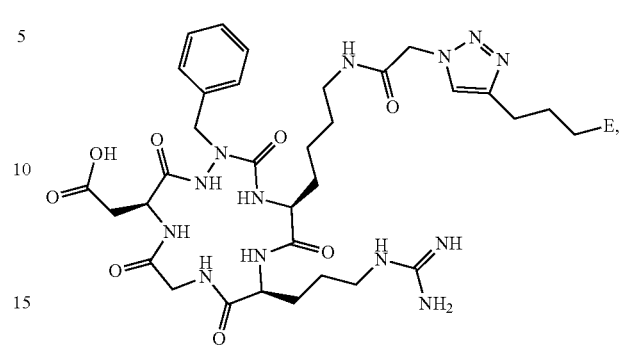

where E is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$, or a pharmaceutically acceptable salt thereof, optionally in the form of a single stereoisomer or mixture of stereoisomers thereof.

* * * * *